United States Patent [19]

Clark, III

[11] 4,362,935

[45] Dec. 7, 1982

[54] FIELD PORTABLE ELEMENT ANALYSIS UNIT

[75] Inventor: Benton C. Clark, III, Littleton, Colo.

[73] Assignee: Martin Marietta Corporation, Bethesda, Md.

[21] Appl. No.: 188,594

[22] Filed: Sep. 18, 1980

Related U.S. Application Data

[63] Continuation of Ser. No. 10,716, Feb. 9, 1979, abandoned.

[51] Int. Cl.$^3$ .................... G01N 23/20; G21K 1/00
[52] U.S. Cl. ........................................ 378/48; 378/98
[58] Field of Search ............................. 250/272, 274

[56] References Cited

U.S. PATENT DOCUMENTS

| | | | |
|---|---|---|---|
| 3,015,027 | 12/1961 | Burst, Jr. et al. | 250/272 |
| 3,101,409 | 8/1963 | Fite . | |
| 3,270,205 | 8/1966 | Ladd et al. . | |
| 3,404,275 | 10/1968 | Martinelli . | |
| 3,511,989 | 5/1970 | Yakubovich et al. | 250/274 |
| 3,859,525 | 1/1975 | Ashe et al. | 250/272 |
| 3,925,660 | 12/1975 | Albert . | |
| 4,063,089 | 12/1977 | Gamba | 250/272 |

FOREIGN PATENT DOCUMENTS 1259220  1/1972  United Kingdom .

OTHER PUBLICATIONS

Toulmin III et al., "Inorganic Chemical Investigation by X-ray Fluorescence Analysis: The Viking Mars Lander", Icarus, vol. 20, pp. 153-178, 1973.

Toulmin III et al., "Report of the Viking Inorganic Chemical Analysis Team: Introductory Statement", Jour. Geophys. Res., vol. 82, No. 28, Sep. 30, 1977, p. 4575.

Clark III et al., "The Viking X-ray Fluorescence Experiment: Analytical Methods and Early Results", Jour. Geophys. Research, vol. 82, No. 28, Sep. 30, 1977, pp. 4577-4594.

Baird et al., "The Viking X-ray Fluorescence Experiment: Sampling Strategies and Laboratory Simulations", Jour. Geophys. Research, vol. 82, No. 28, Sep. 1977, pp. 4595-4624.

Toulmin III et al., "Geochemical and Mineralogical Interpretation of the Viking Inorganic Chemical Results", Jour. Geophys. Res., vol. 82, No. 28, Sep. 1977, pp. 4625-4634.

Clark, "X-ray Fluorescence Geochemical Analysis on the Surface of Mars", Nuclear Methods in Mineral Exploration and Production, Chap. 4, pp. 93-112, Elsevier Scientific Publishing Co., 1977.

"EDAX ® 707B Energy Dispersive XRay Analyzer with Microedit ® for Qualitative, Semiquantitative and Quantitative Analysis", EDAX International (Advertising Brochure), Jul. 1974, pp. 1-11.

Primary Examiner—Alfred E. Smith
Assistant Examiner—T. N. Grigsby
Attorney, Agent, or Firm—Yount & Tarolli

[57] ABSTRACT

A field portable X-ray fluorescent spectrometer is described including a multichannel analyzer (2) and a plurality of interchangeable sensor heads (4). Each sensor head includes a shutter (100) which, when open, permits one of several radiation sources (80, 82) to irradiate a material to be analyzed. The returned radiation is detected by a corresponding detector (86, 90), which provides corresponding data in response. This shutter has calibration plaques attached to it so that, when closed, the plaques are exposed to the radiation sources and return radiation having selected energy distributions to the detectors. The multichannel analyzer uses the resulting detector data to calibrate the sensor head. Each sensor head includes circuitry (290) for identifying itself to the multichannel analyzer. The analyzer automatically adapts its operation in accordance with this identification. When the shutter is open, the multichannel analyzer utilizes the detector data to accumulate an energy spectrum of the material being analyzed, and displays the spectrum on a display screen (12). A cursor control (28) allows the operator to move a cursor along the displayed spectrum. A display (32) is automatically provided with a display of the symbol of the element, if any, having its major spectral peak at the position identified by the cursor. Secondary indications identify other positions along the spectrum at which peaks would appear if the element were present. Memory (202) is provided for storing a number of reference spectra, any of one of which may be displayed on the screen along with the acquired spectrum for comparison purposes. The memory (202) also stores previously acquired spectra for later analysis. The analyzer also includes other operational features, such as normalization, window control, and ratio and concentration determination, to permit the operator to quantitatively analyze materials in the field.

27 Claims, 19 Drawing Figures

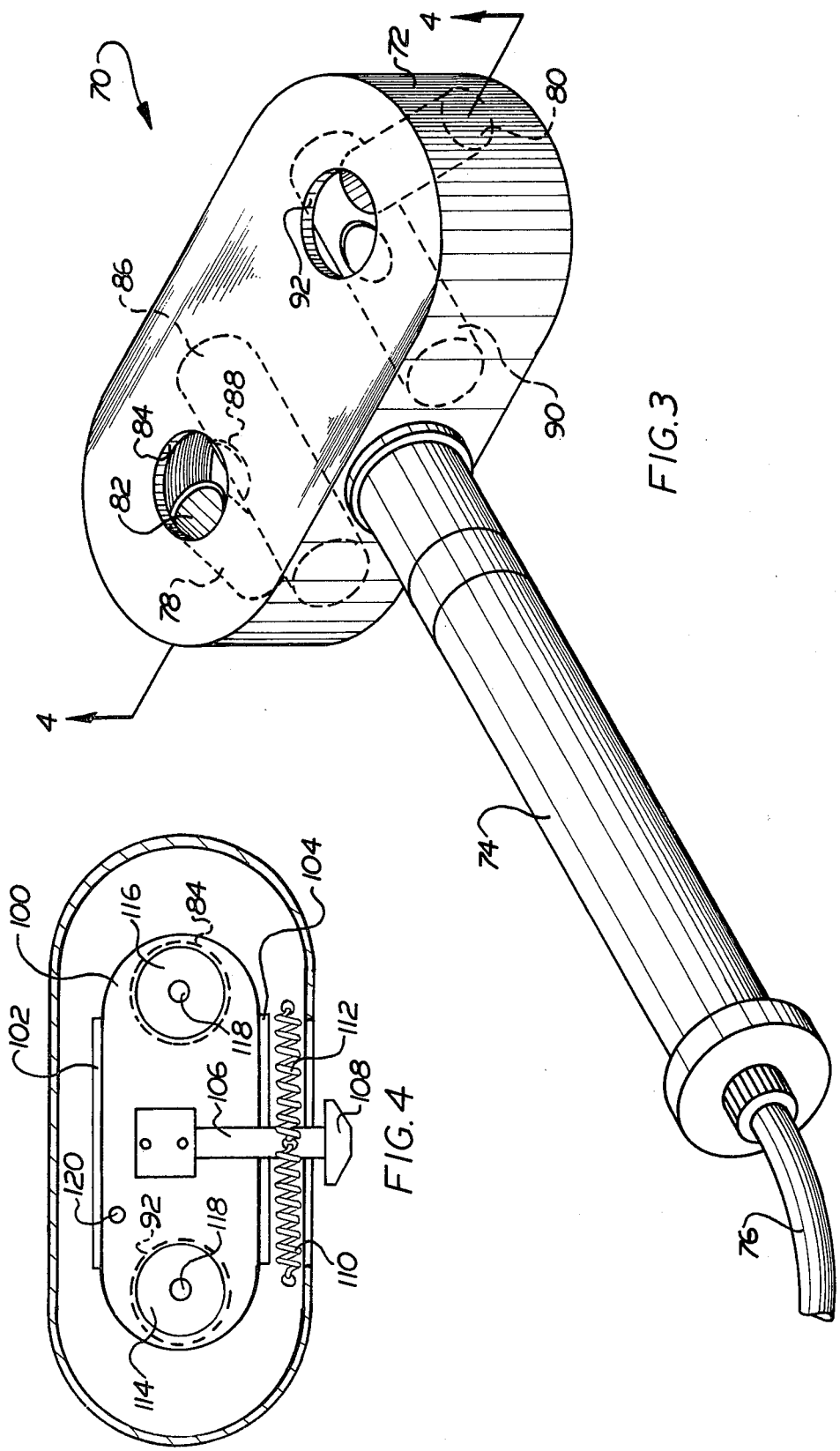

SENSOR HEAD

FIG. 9 ANALYZER CONTROLS

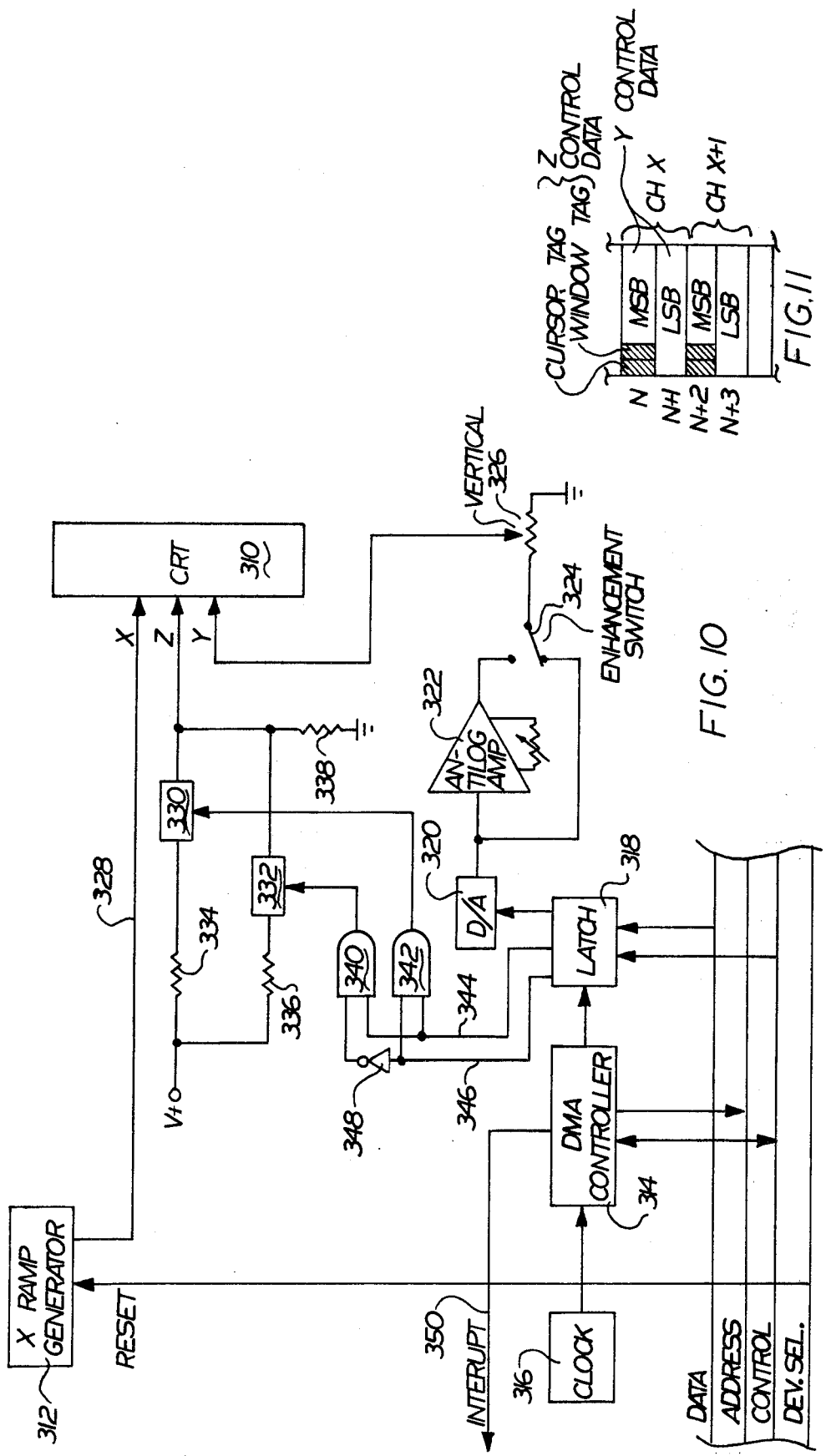

DATA ACQ. OPS

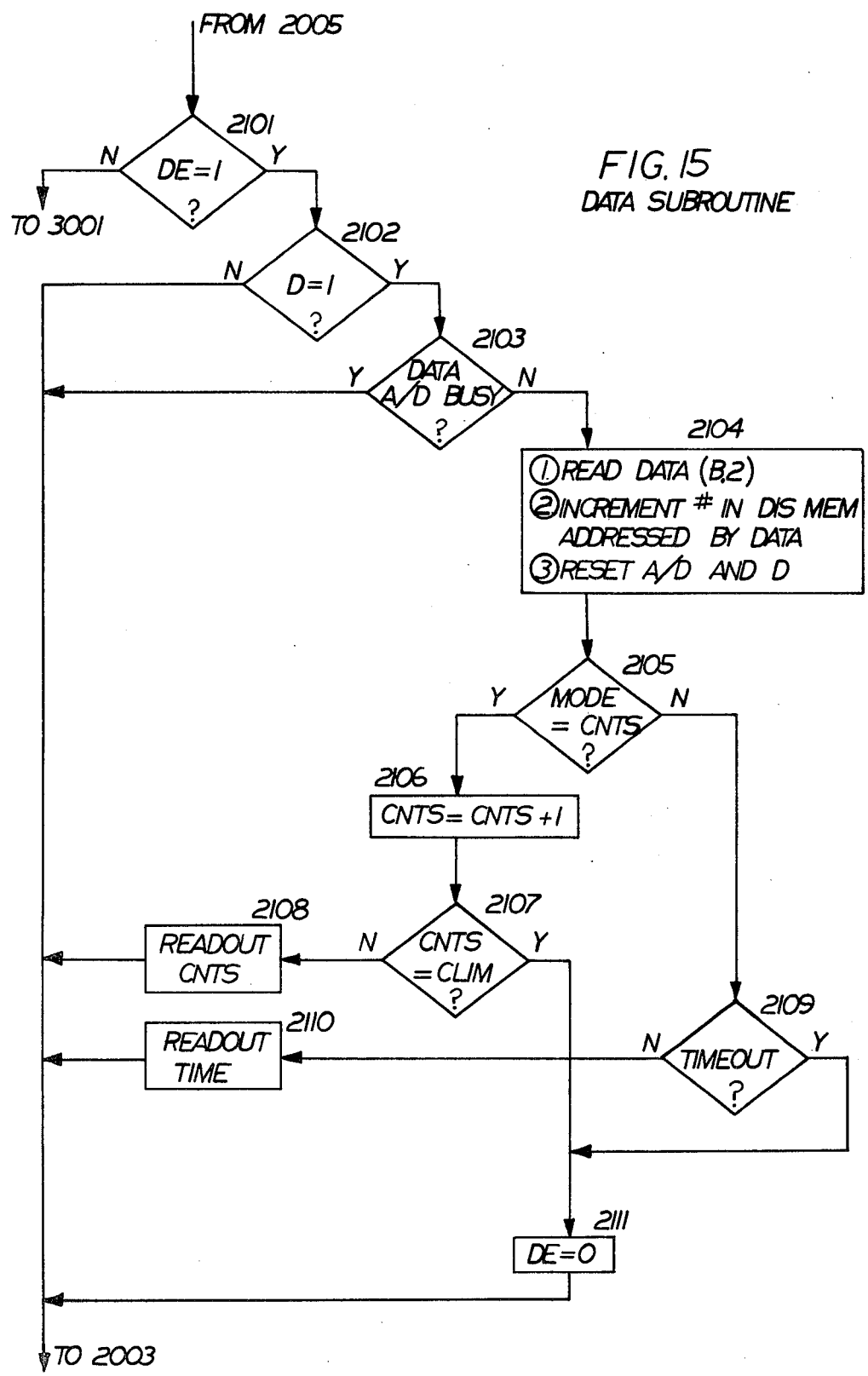

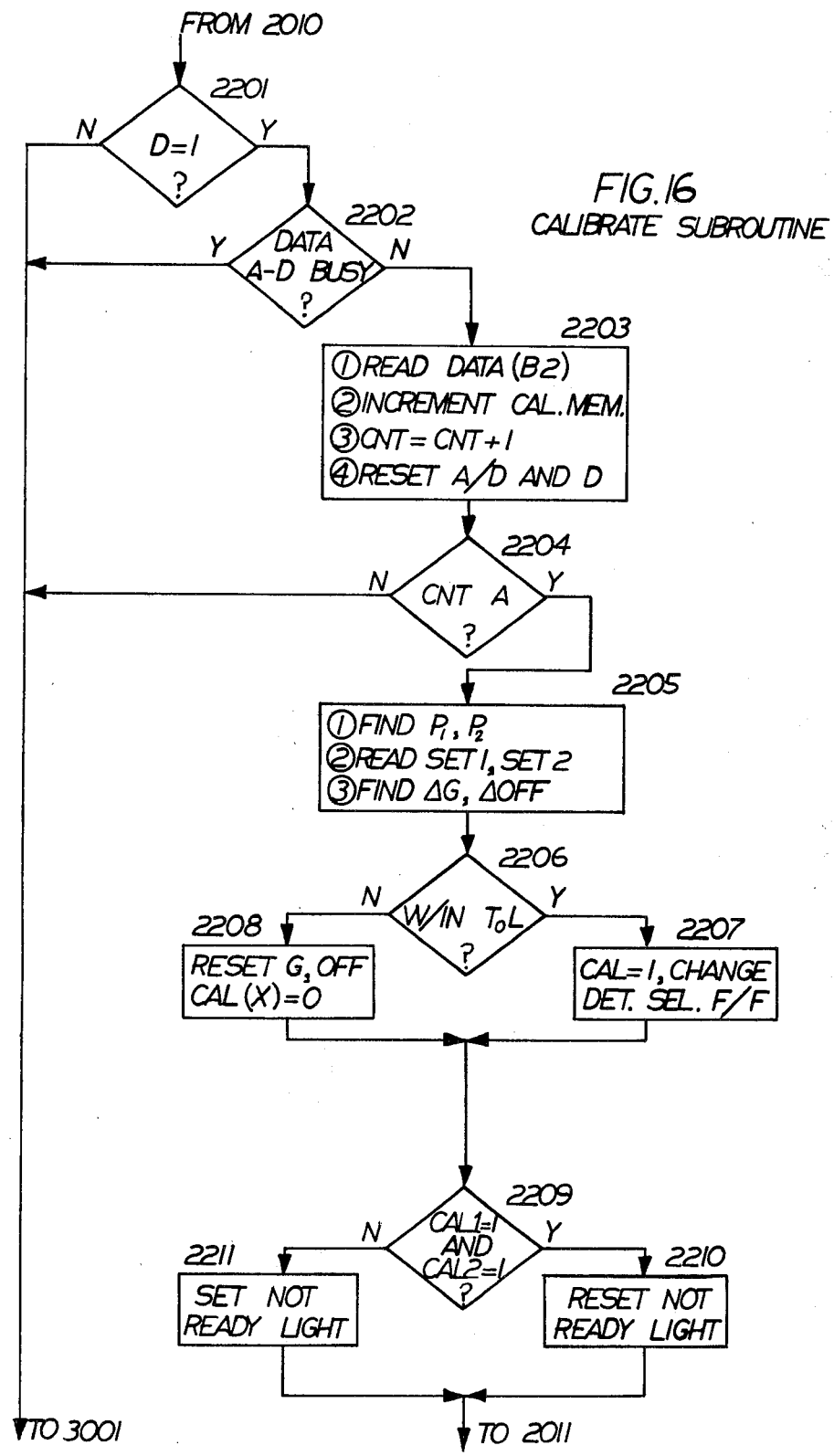

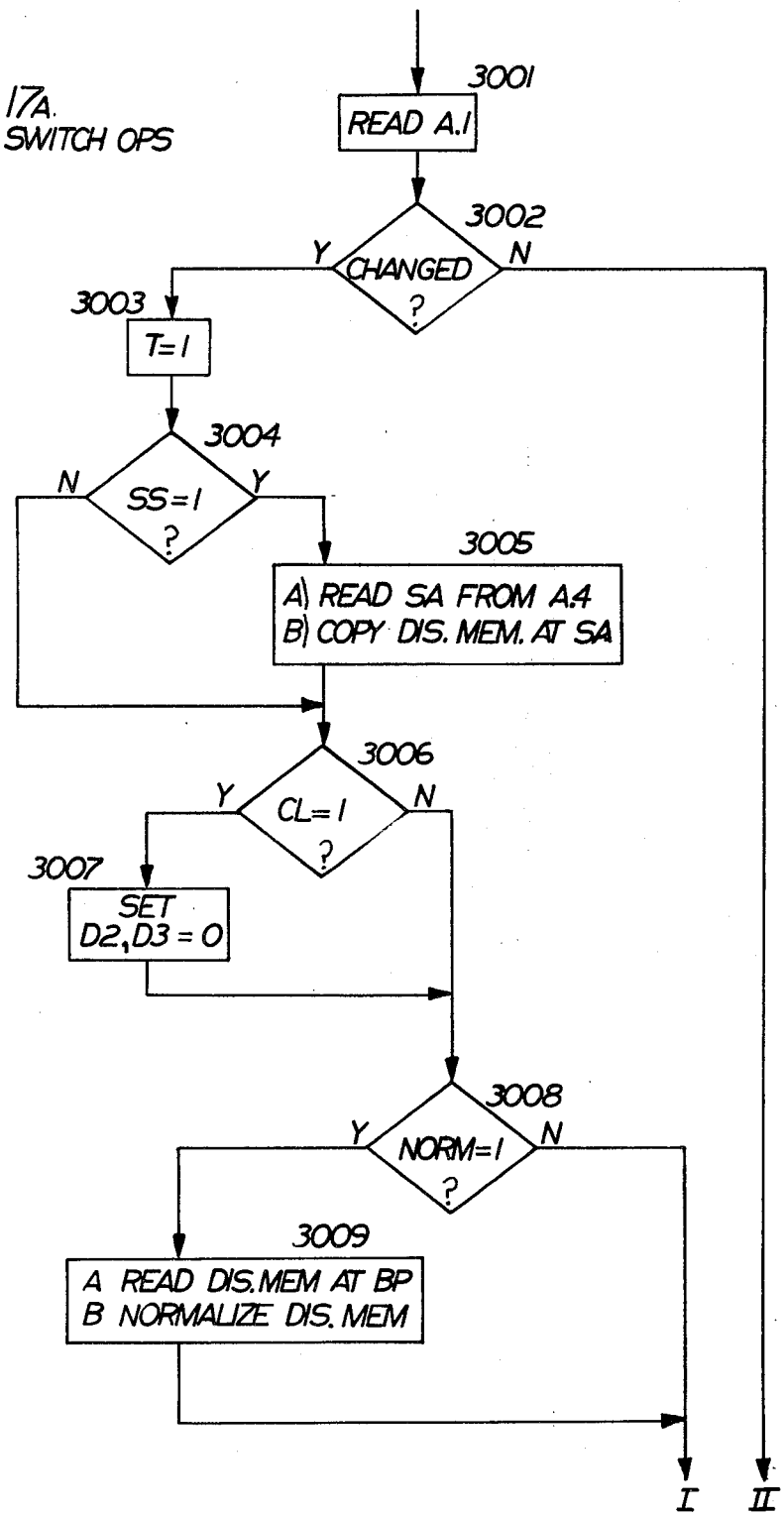

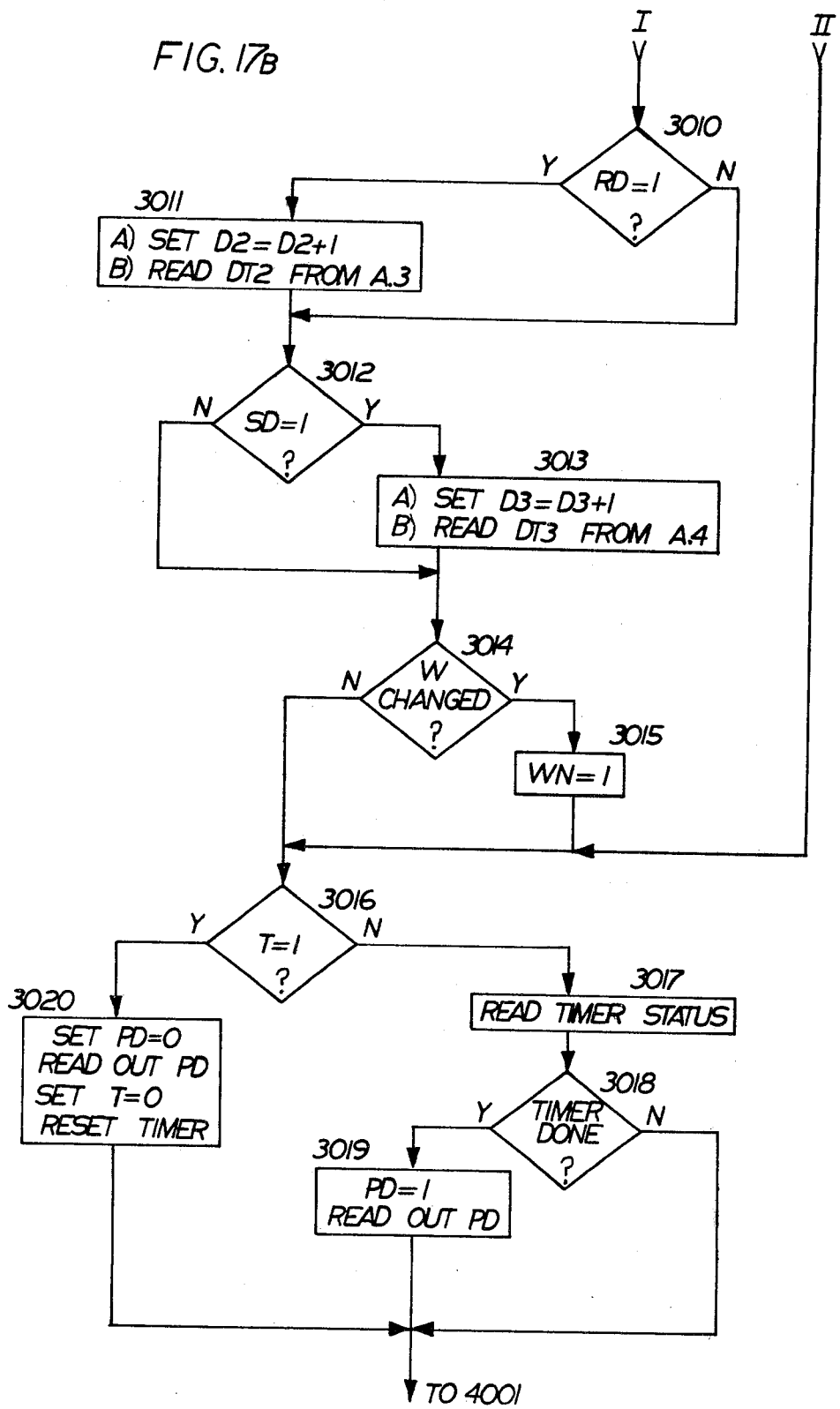

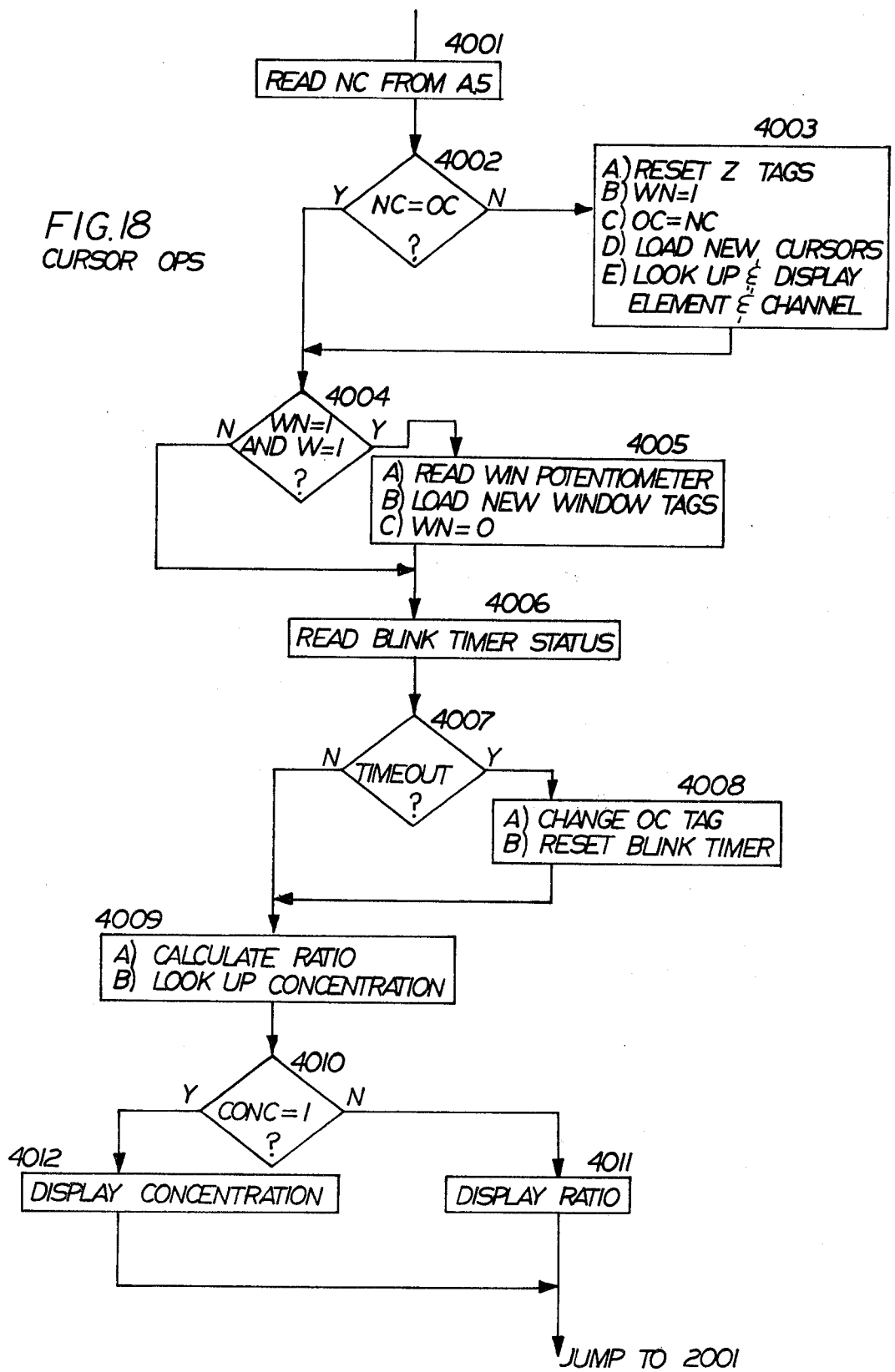

FIELD PORTABLE ELEMENT ANALYSIS UNIT

This is a continuation, of application Ser. No. 010,716 filed Feb. 9, 1979, now abandoned.

BACKGROUND AND FIELD OF THE INVENTION

The present invention relates to element analysis systems, and more particularly to a field portable X-ray fluorescent spectrometer.

X-ray fluorescent spectrometers have long been used to analyze the elemental composition of mineral samples taken during geological surveys. In operation, the unknown mineral samples are irradiated in order to cause them to fluoresce, and the resulting fluorescent X-ray radiation is analyzed with a multichannel radiation analyzer. The multichannel analyzer accumulates a spectrum representing the energy distribution of the fluorescent radiation. The profile of the energy spectrum thus obtained will be determined by the elemental composition of the sample. Thus, the elemental composition of the sample can then be determined by comparing the spectrum with other spectrums obtained from samples of known composition.

Due to the not inconsiderable size of these X-ray fluorescent spectrometers, the practice has heretofore been to install the X-ray fluorescent spectrometer at a fixed location, often quite distant from the area being surveyed. Specimens collected in the field thus had to be transported to the spectrometer for analysis. Furthermore, the specimens often had to be processed (as by pulverizing them) before analysis could begin. The pinpointing of a particular mineral concentration was thus a lengthy process, since it might be necessary to make multiple trips to the survey site in order to obtain samples from slightly different areas than those from which the initial samples had been collected. To reduce survey time, then, it was important that the surveyor collecting the samples draw upon his own experience to provide a visual, first order analysis of the mineral content of the samples being collected. Experience of the surveyor was therefore a factor of considerable importance.

Several miniature element analysis units utilizing the property of X-ray fluorescence were developed for use in space exploration, and are now being used in the two Viking landers presently operating on the surface of the planet Mars. Unfortunately, these X-ray fluorescent spectrometers were designed solely to acquire and transmit raw spectrographic data, and could not be used to provide a meaningful analysis of mineral samples in a field portable, man-in-the-loop system. Thus, the data acquired by the Viking Mars landers is processed in a large scale, Earth-based data processing computer.

SUMMARY OF THE INVENTION

The present invention provides a field-portable element analysis and material identification unit which may be used in a man-in-the-loop system to provide semi-quantitative and qualitative information regarding the composition of unprocessed material samples. This element analysis unit not only permits semi-quantitative analysis of the sample being examined, but also permits the comparison of the spectrum of a given sample with a large number of reference samples, as well as storage of the spectrum for later analysis. In addition, the unit includes plural, interchangeable sensor heads, each having different radiation sources therein, so as to permit analysis of a wide range of elements.

It is an object of the present invention to provide a field-portable element analysis and materials identification unit which permits semi-quantitative analysis of unprocessed material samples.

It is another object of the present invention to provide a field-portable element analysis unit which incorporates calibration features to free the unit from drift and gain errors.

It is still another object of the present invention to provide an element analysis unit having a number of interchangeable sensor heads, each employing one or more different radiation sources and associated detectors, so that the unit has the flexibility to perform analysis of a wide range of mineral compositions.

It is even another object of the present invention to provide an element analysis unit which provides a visual display of the energy spectrum of fluorescent X-rays emitted by an irradiated sample, and which includes a cursor movable along the spectrum, with the unit providing an indication to the operator of the element which has its major peak at that position on the spectrum at which the cursor is located.

It is another object of the present invention to provide an element analysis unit in accordance with the foregoing object, wherein the unit also provides one or more other indicators positioned at locations along the spectrum corresponding to the positions of peaks of reference spectrums so as to permit ready comparison between the positions indicated by those indicators and the peaks of the sample spectrum being analyzed.

BRIEF DESCRIPTION OF THE DRAWINGS

The foregoing and other objects and advantages of the present invention will become more readily apparent from the following detailed description, as taken in conjunction with the accompanying drawings, wherein:

FIG. 3 is a perspective illustration of the sensor head of the element analysis unit of FIG. 1;

FIG. 4 is a more detailed illustration of the sensor head of FIG. 3, showing the arrangement of the shutters therein;

FIG. 9 is a circuit schematic of the analyzer control block of the block diagram of FIG. 6;

FIG. 10 is a more detailed illustration of the display circuitry of the block diagram of FIG. 6;

FIG. 11 is a representation of the manner in which information is stored in the display memory;

FIGS. 13–19 are flow charts which illustrate in greater detail the manner of operation of the circuitry of the block diagram of FIG. 6.

DETAILED DESCRIPTION

Figure 1:
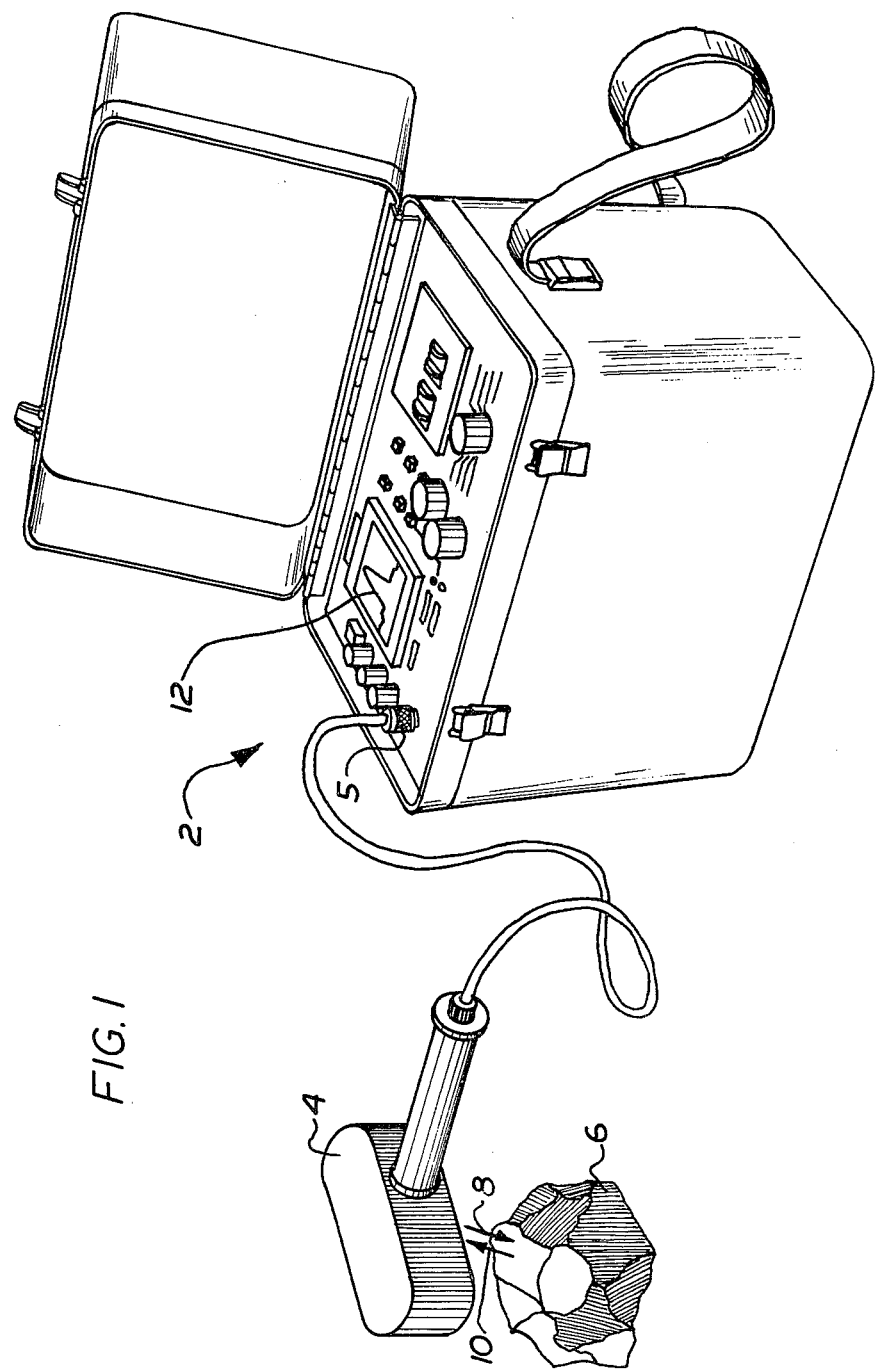
FIG. 1 is an illustration of an element analysis unit in accordance with the teachings of the present invention.

Referring first to FIG. 1, the element analysis unit broadly consists of two components; a multichannel analyzer 2 and a hand-held sensor 4. The two units are coupled together by a conventional multiconductor connector 5. This connector permits easy disconnection of the sensor head 4 from the analyzer 2, and the substitution of a different sensor head having different detectors and radioactive sources. The unit is entirely self contained, and includes an internal battery in order to provide the power necessary for all normal operations. The unit is mounted in a suitable carrying case and thus may be readily carried about in the field without undue discomfort to the operator.

In order to analyze a mineral sample 6, the sensor head will be appropriately positioned over the sample 6, and a shutter on the sensor head will be opened so as to expose the sample to a beam of radiation 8 generated by a radioactive source located within the sensor head. A detector, also located within sensor head 4, will detect the fluorescent radiation 10 emitted by the sample. For each detected particle of fluorescent radiation, the sensor head 4 provides a corresponding digital signal to the multichannel analyzer 2. Each of these digital signals will have a binary value indicating the energy of the corresponding detected X-ray.

The multichannel analyzer 2 sorts these digital words according to binary values, and provides a display graphically indicating the number of pulses which have been processed for each energy value. The multichannel analyzer 2 may be simply characterized as including one counter for each possible binary value of the digital signals supplied by the sensor head. Each time a digital signal is provided to the multichannel analyzer, the number within the counter identified by the binary value of that signal will be incremented. As these counts are being accumulated, the contents of all of the counters will be sequentially displayed at consecutive horizontal positions across a display screen 12 to produce an energy spectrum thereon. The vertical height of this spectrum at any given horizontal position along the display screen will indicate the number of counts accumulated in the counter corresponding to that horizontal position, and thus to that particular energy channel.

Figure 2:
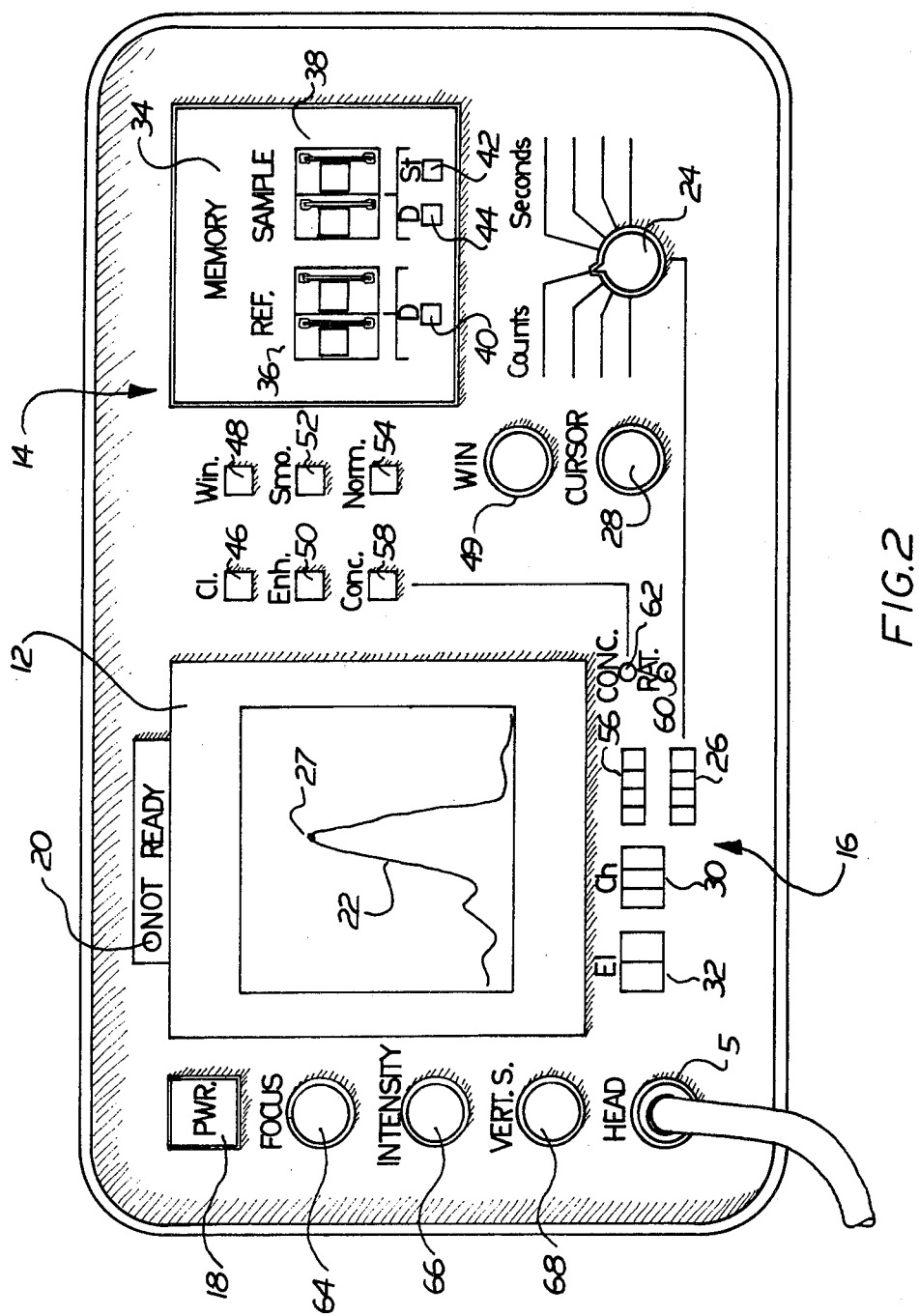
FIG. 2 is a plan view of the control panel of the multi-channel analyzer utilized in the element analysis unit of FIG. 1.

The control panel of multichannel analyzer 2, shown more clearly in FIG. 2, broadly includes a display screen 12, as well as a number of control switches 14 and alphanumeric displays 16. Displays 16 will preferably be of the liquid-crystal variety (LCD's) to minimize power consumption thereby. A power switch 18 controls the application of power to the control circuitry located within the multichannel analyzer 2, and to the various displays associated therewith. Upon the initial application of power to the unit the control circuitry will initialize the operation of the element analysis unit in preparation for the acquisition of data. During this warm up period, a NOT READY light 20 located immediately above the display screen 12 will be illuminated. Upon conclusion of the warm up and initialization cycles, the NOT READY light 20 will switch off, indicating that the unit is prepared for normal operation. The operator may then actuate the shutter on the sensor head, automatically resetting the display memory and initiating the accumulation of data by the multichannel analyzer. During the accumulation of data, the display screen 12 will be periodically updated so that the spectrum 22 provides a continuous indication of the spectrum being accumulated by the sensor head.

A multi-position rotary switch 24 is included to control the interval of time during which data is accumulated. This switch 24 may be switched to one of eight different positions. When in one of the four rightward positions (as viewed in FIG. 2), the multi-channel analyzer will accumulate data for a fixed interval of time, set by the one of the four switch positions at which the switch 24 is located. When in one of the four leftward switch positions, however, the analyzer will accumulate counts for an arbitrary interval of time, until a specified number of counts has been accumulated therein. Again, the number of counts required to conclude the acquisition of a particular sample spectrum is determined by the one of the four switch locations at which the switch 24 is located. A four digit readout 26 is included to provide a numerical display of the number of seconds or counts which have transpired in a given sample spectrum acquisition run. Of course, the operator may also conclude the taking of data samples simply by releasing the shutter on the sensing head, thereby automatically disabling the taking of further data.

As stated previously, the profile of the sample spectrum thus obtained will be determined by the elemental composition of the mineral sample. More specifically, the position (i.e. energy channel) of the various peaks in the spectrum indicates the composition of the mineral sample, since each element fluoresces at discrete energies characteristic to that element. The height of each peak, on the other hand, is determined by the number of particles detected in that energy channel. This, in turn, is proportional to the quantity present of the element producing that peak. The spectrum therefore provides both qualitative and quantitative information as to the content of the mineral sample being analyzed.

The multichannel analyzer 2 generates a cursor 27 movable along the spectrum 22 in order to identify a particular channel therealong. This cursor is generated by brightening the portion of the spectrum 22 associated with the energy channel at which the cursor is located. This cursor may be moved from channel to channel by means of a cursor control knob 28. The number of the channel upon which the cursor is located will be readout upon a numerical display 30. Another display 32 provides an alphanumeric readout of the symbol of the element having its major peak on the channel upon which the cursor is located. If no element has a peak at that channel, then the element display 32 will be blank.

One or more additional channels may also be highlighted. This additional highlighting will hereinafter be referred to as "secondary" indicators. These secondary indicators identify the energy channels where other peaks exist in the spectrum of the element whose major peak is identified by the location of the cursor. These peaks may be K, L, or M peaks, escape peaks, etc. Thus, if an element had its major peak in the energy range covered by the display, and also had one or more other peaks in that range, all of these peak channels would be highlighted whenever the cursor was positioned at the channel of the major K peak. To permit the operator to readily differentiate between the highlighting indicating the cursor and that representing a "secondary indication" the cursor will blink on and off whenever positioned at a channel corresponding with some elements major peak.

In order to facilitate the analysis of a mineral sample spectrum, the element analysis unit also provides for the display of multiple spectrums upon the display screen 12 at one time. These additional spectrums will be recalled from a solid state memory associated with the element analysis unit, and may be either temporarily or "permanently" stored within the unit. Thus, this solid state memory includes a read-only memory (ROM) section providing "permanent" storage of a number of reference spectrums of known minerals and also includes a random-access memory (RAM) section for temporary storage of a plurality of spectrums previously acquired from other mineral specimens.

The storage and display of spectrums is controlled by memory controls 34. These memory controls include two sets of thumbwheel switches 36 and 38, each of which may be set to identify any one of up to one hundred different spectrums stored in memory. The thumb wheel switches 36 provide access to the reference spectrums stored within the memory of the element analysis unit. The display of any one of these reference spectrums may be accomplished by setting the thumb wheel switches 36 to the appropriately numbered memory location, and then depressing a DISPLAY switch 40 associated therewith. The element analysis unit will respond to this by displaying the appropriate reference spectrum upon the display screen 12 along with the spectrum 22 acquired from the mineral specimen presently being examined. This spectrum may be deleted from the display by again depressing switch 40.

Similarly, the thumb wheel switches 38 may be set to identify any one of up to one hundred different temporary storage locations within the memory of the element analysis unit. When a STORE button 42 is depressed, the sample spectrum 22 presently being displayed upon the screen 12 will be stored in the memory location identified by the position of thumb wheel switches 38. Any sample spectrum which has been stored in this fashion may be recalled from the temporary memory by appropriate setting of thumbwheel switches 38 and depressing a DISPLAY button 44, also associated with the thumbwheel switches 38. Again, this sample spectrum may be removed from the display by depressing switch 44 once more.

The screen 12 may therefore display as many as three different spectrums at one time: the spectrum of a sample presently being analyzed, a reference spectrum stored in memory within the element analysis unit, and a spectrum of a previously acquired sample spectrum, also stored in memory.

The spectrum 22 of the sample being analyzed will be erased from the screen 12 every time the shutter of the sensor head is opened. The other traces, however, will remain upon the screen until the respective display button is depressed once more, or a CLEAR switch 46 is pressed. This CLEAR switch operates to erase the other traces from the screen, but does not effect the display of the spectrum 22 of the sample being analyzed.

Various other switches 48, 50, 52 and 54 are provided for controlling various other characteristics of the display provided on display screen 12. A WINDOW switch 48, when pressed, will cause the multi-channel analyzer to blank the display of all of spectrum 22 except that portion which is within a selected number of channels of the position of the cursor. This will have the effect of minimizing extraneous confusion during those operations in which only a single peak is of substantial interest in the entire spectrum 22. The WINDOW feature may also be cancelled by again depressing the WINDOW switch 48. A window potentiometer 49 sets the width of the display window, permitting operator control thereof.

The peaks of the spectrum 22 may be enhanced by depressing an ENHANCEMENT switch 50. When this button is depressed, an anti-log amplifier is switched into the Y channel of the display screen 12 (which is a cathode ray tube (CRT) in the described embodiment), causing the peaks of the spectrum 22 to be emphasized.

A smoothing function, controlled by switch 52, is provided for use in conjunction with the enhancement function, since otherwise rather bizzare and meaningless exaggeration of statistical outliers will result. This smoothing function alters the manner in which data is acquired by the multi-channel analyzer, so as to eliminate, to the extent possible, the statistical nature of the spectrum.

A normalization function, controlled by a normalization switch 54, is also provided for use in conjunction with the enhancement and smoothing functions. This normalization function automatically normalizes the display by dividing the count for each channel by a number proportional to the number of counts in the backscatter peak.

The unit includes provisions for accomplishing semiquantitative analysis of samples by examining peak heights. The peak heights are not sufficient by themselves, however, to determine the quantitative constituents of the mineral specimen. This is because the height of any given peak within the spectrum will depend upon, among other factors, the strength of the radiation source, the distance from the source to the sample (and the sample to the detector), the density of the sample and its X-ray absorption characteristics, the particle size granularity, and surface roughness of the sample.

The effect of these factors can be greatly reduced or eliminated by evaluating the fluorescent peaks of the spectrum relative to the intensity of backscatter radiation intensity. For example, if the sensor head is not placed directly on the sample, a lower rate of counting of fluorescent rays will occur than if the device were closer. The backscatter intensity (resulting both from compton radiation and coherently scattered radiation) from the sample will, however, also be less by the same scale factor. The element analysis unit of the present invention utilizes this effect to provide a semiquantitative measure of the abundance of selected elements. Since the uncertainties due to the factors given above are greatly reduced by measuring the intensities relative to the backscatter peak, the need to process and prepare the sample prior to analysis is essentially eliminated.

A numerical readout 56 is included to provide a visual indication to the operator of the results of this analysis. The multichannel analyzer will indicate in this numerical read out either the ratio of a given peak relative to the backscatter peak, or the concentration of the given element. Which of these functions is being performed will depend upon the position of a CONCENTRATION switch 58. When this switch is in one position, the ratio light 60 will be illuminated, and the read out 56 will provide a read out of the number of counts in the channel upon which the cursor is presently positioned, divided by the number of counts in a reference, backscatter channel. When the concentration switch 58 is in its second position, however, the ratio light 60 will be darkened, and a concentration light 62 will instead be illuminated. The numerical read out 56 will then provide a direct read out of the concentration of the given element within the mineral composition.

The manner in which the CONCENTRATION function is accomplished will be described more fully hereinafter, however broadly it may be described as follows. The analyzer control circuitry has a number of look-up tables stored therein, each of which plots fluorescent backscatter ratio on one axis versus the concentration of a selected element on the other axis. These look-up tables are indexed according to both mineral composition, and element peak. The operator will select an appropriate look-up table by setting the thumbwheel switch 36 at the value addressing the reference spectrum most nearly approximating the sample spectrum 22, and positioning the cursor at the peak of the element of interest. The analyzer examines the position of the reference thumbwheel switch 36 and the position of the cursor, and refers to the appropriate look-up table upon this basis. The ratio value determined for that particular cursor location is then used to address the selected look-up table and thus provide a read-out of the concentration of the element within the sample under study.

In addition to the controls described above, the multi-channel analyzer also incorporates two potentiometers 64 and 66 for respectively controlling the focus and intensity of the spectrums displayed on the display screen 12. A third potentiometer 68 permits operator modification of the vertical scale of the spectrum 22. Thus, by suitable adjustment of the vertical scale knob 68, the vertical scale of the spectrum 22 may be expanded or reduced.

FIG. 3 illustrates one embodiment of the sensor head for use in conjunction with the multi-channel analyzer shown in FIG. 2. This sensor head 70 includes a head assembly 72 and a handle assembly 74, and is connected to the multi-channel analyzer through a suitable length of multi-conductor cable 76.

In this embodiment, the head assembly 72 has two sources of nucleonic radiation 78 and 80 mounted therein. Nucleonic source 78 is enclosed within a radiation shielded casing having an opening 82 therein. The nucleonic source 78 is oriented within the head assembly 72 so that the loosely collimated beam of nucleonic radiation emitted through the opening 82 in the casing of source 78 will pass through a suitable opening 84 in the housing of the head assembly 72. This opening 84 will normally be blocked by a shutter, not shown in this figure.

A detector 86 is provided adjacent the opening 84 to provide detection of the nucleonic particles fluoresced by the mineral speciman against which the sensor head assembly 72 is placed. In the illustrated embodiment, this detector 86 is a gas-filled proportional counter (PC) detector. Other types of detectors (such as solid state mercuric iodide detectors) could, of course, be used instead if desired. This PC detector 86 has a foil window 88 therein through which the nucleonic particles are to pass. The detector 86 will be oriented so that the opening 88 is also adjacent the opening 84 in the head assembly 72, but is not within the direct line of radiation emitted from the source 78.

PC detector 86 consists essentially of a chamber filed with a specific gas. Two electrodes are placed within this chamber, and a high voltage is applied between them so that a high potential electrostatic field exists within the chamber. When a nucleonic particle passes through the chamber, the gas therein will be ionized so that a trickle of current will temporarily flow between the two electrodes. This causes a momentary change in the current flow through the electrodes, which is sensed by a charge sensitive circuit to be described in detail hereinafter.

The second source 80 also has a PC detector 90 associated therewith. As before, the windows in the source 80 and the PC detector 90 are both pointed towards an opening 92 in the housing of the head assembly 72.

Again, a shutter will normally cover the opening 92. Sources 78 and 80 will be provided with different sources of nucleonic radiation, so that the operator may select one or the other source simply by operating the shutter to expose one of the two openings 84, 92 associated with the sensor head 72. Source 78 may, for example, be a Fe-55 radiation source, whereas source 80 may be a Cd-109 radiation source. Another of the interchangeable sensor heads could instead use Am-241 and Co-57 radiation sources. These sources are selected so that energy of the x-rays used to irradiate the sample are only slightly above to several times the energies of the K, L and M lines of interest. It will be noted that the orientation of the two sources 80 and 82 is such that the beams of radiation emitted therefrom point generally away from the nearer edge of the head assembly 72. This is done for reasons of operator safety; most of the backscattered radiation will now impinge on the head assembly 72, rather than passing beyond the boundaries thereof and thus possibly posing a radiation hazard to the operator.

FIG. 4 is a section taken generally along lines 4-4 of FIG. 3, and illustrates the shutter arrangement for selectably covering or uncovering the openings 84 and 92 associated with the head assembly 72 of FIG. 3. A single shutter effects the blocking and unblocking of both openings. This shutter is comprised of a single, essentially rectangular tungsten coated plate 100 which rides along longitudinal notches in two rails 102 and 104 on either side of the openings 84 and 92. The shutter 100 may therefore be moved leftward or rightward (as viewed in FIG. 4) along these rails. A lever arm 106 is rigidly affixed to the shutter 100, and extends through a slot in the housing of sensor head 72. A button 108 is attached to the exterior portion of the lever arm 106. The operator may uncover the opening 84 by moving the button 108 to the leftward, as viewed in FIG. 4, and may uncover the opening 92 by instead moving the button 108 in a rightward direction, as viewed in FIG. 4. Two springs 110 and 112 are attached between the lever arm 106 and the housing of the sensor assembly 72 so as to spring bias the shutter 100 in a central position, wherein both of openings 84 and 92 are covered by the shutter 100.

When in this central position, two calibration plaques 114 and 116, attached to the shutter plate 100, will be located essentially concentrically over the openings 84 and 92. These calibration plaques are circular discs of quartz glass, with iron dots 118 bonded to the center thereof. These calibration plaques are provided to permit rapid and accurate calibration of the gain and offset of the multi-channel analyzer, through the operation of circuitry which will be described hereinafter. Essentially, these calibration plaques provide a known spectrum which should have peaks in predetermined positions along the spectrum 22 displayed on display surface 12. When the shutters are in the fully closed position illustrated in FIG. 4, these calibration plaques will be exposed to the X-rays provided by the X-ray sources, and should therefore provide spectrums having the predetermined form. The calibration spectra will each include at least two peaks, with one preferably at the upper end of the displayed energy range and the other at the lower end of the displayed energy range. In the embodiment being described, one of these peaks is represented by the backscattered radiation, with the other being a peak in the spectrum of the calibration plaque material. If the peaks provided by the calibration spectrum do not occur in the expected places, the gain and offset of the instrument will be adjusted accordingly. Although this calibration procedure is performed automatically in the described embodiment, manual adjustment of the gain and offset could as easily be used. These calibration plaques therefore provide a convenient and easy measure of the calibration of the instrument.

Three microswitches, not shown in FIG. 4, are associated with the shutter plate 100 and are provided in order to sense its actual position. Two microswitches are provided at the extreme right and leftward extent of travel of the shutter plate 100, and provide signals indicative of whether one of the openings 84 or 82 is exposed. The third switch is provided adjacent the position which a hole 120 in the shutter plate 100 will occupy when the shutter plate is in its central position. This switch senses the presence or absence of the hole 120 at this location, and thus the output thereof will indicate whether or not the shutter plate 100 is in its central position (i.e. whether both of openings 84 and 92 are covered).

Figure 5:
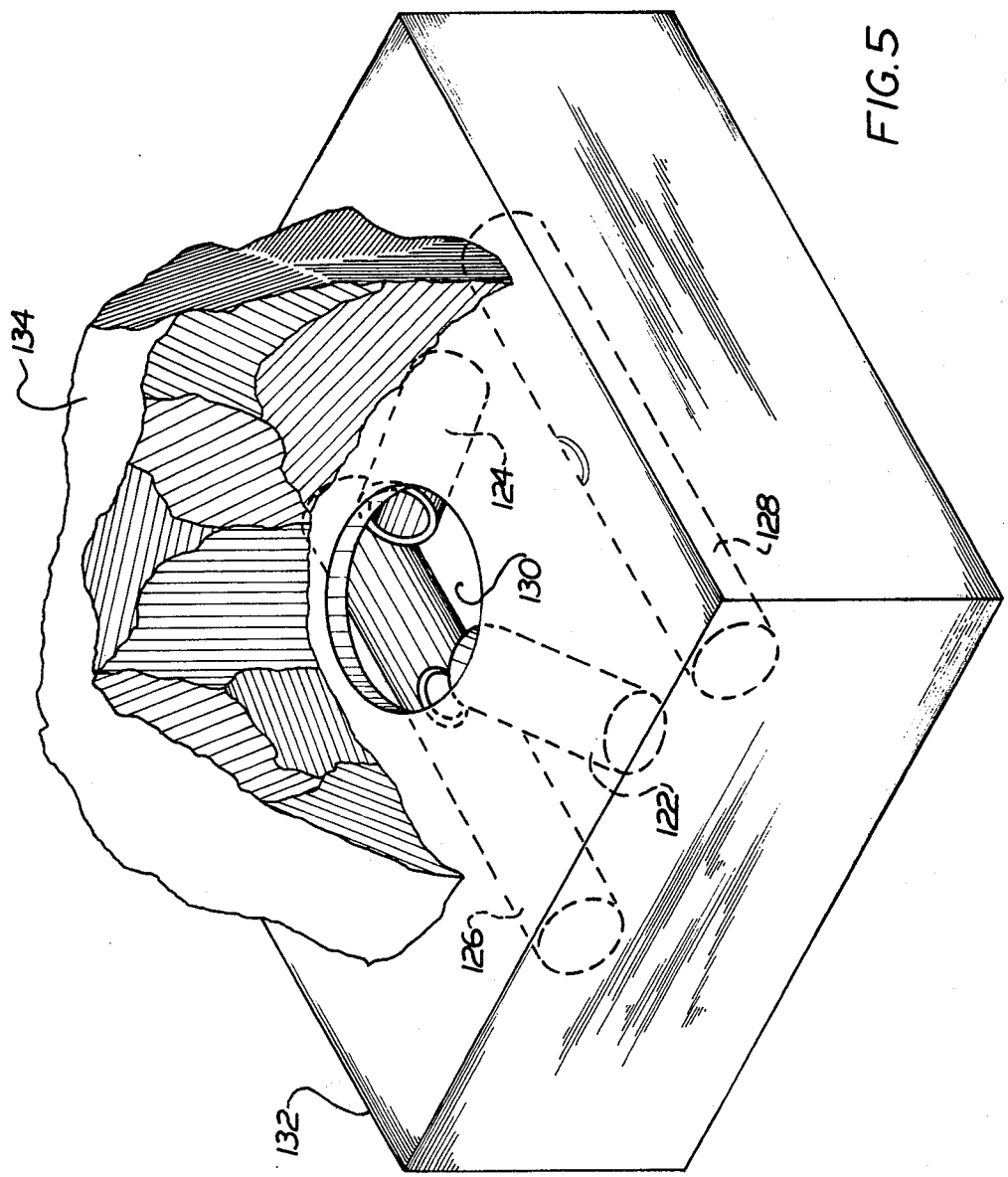
FIG. 5 is a partly schematic perspective illustration of another embodiment of a sensor head for use in conjunction with the element analysis unit of FIG. 1.

FIG. 5 illustrates another embodiment of the sensor head assembly 10. In this embodiment, two sources 122 and 124 are again provided, each again accompanied by a corresponding PC dectector 126, and 128. Unlike the previous embodiment, however, only a single opening 130 is provided in the exterior of the housing 132 of the sensor head assembly. Both of the sources 122 and 124 are oriented with respect to the opening so that the loosely collimated beams of X-rays which are provided thereby are directed outward through the opening 130. Similarly, the windows in the PC detectors 126 and 128 are oriented facing the opening 130 so as to receive the fluorescent radiation emitted by the sample 134 positioned adjacent the opening 130. Again, a shutter assembly will be provided, in this case having only a single calibration plaque associated therewith.

Figure 6:
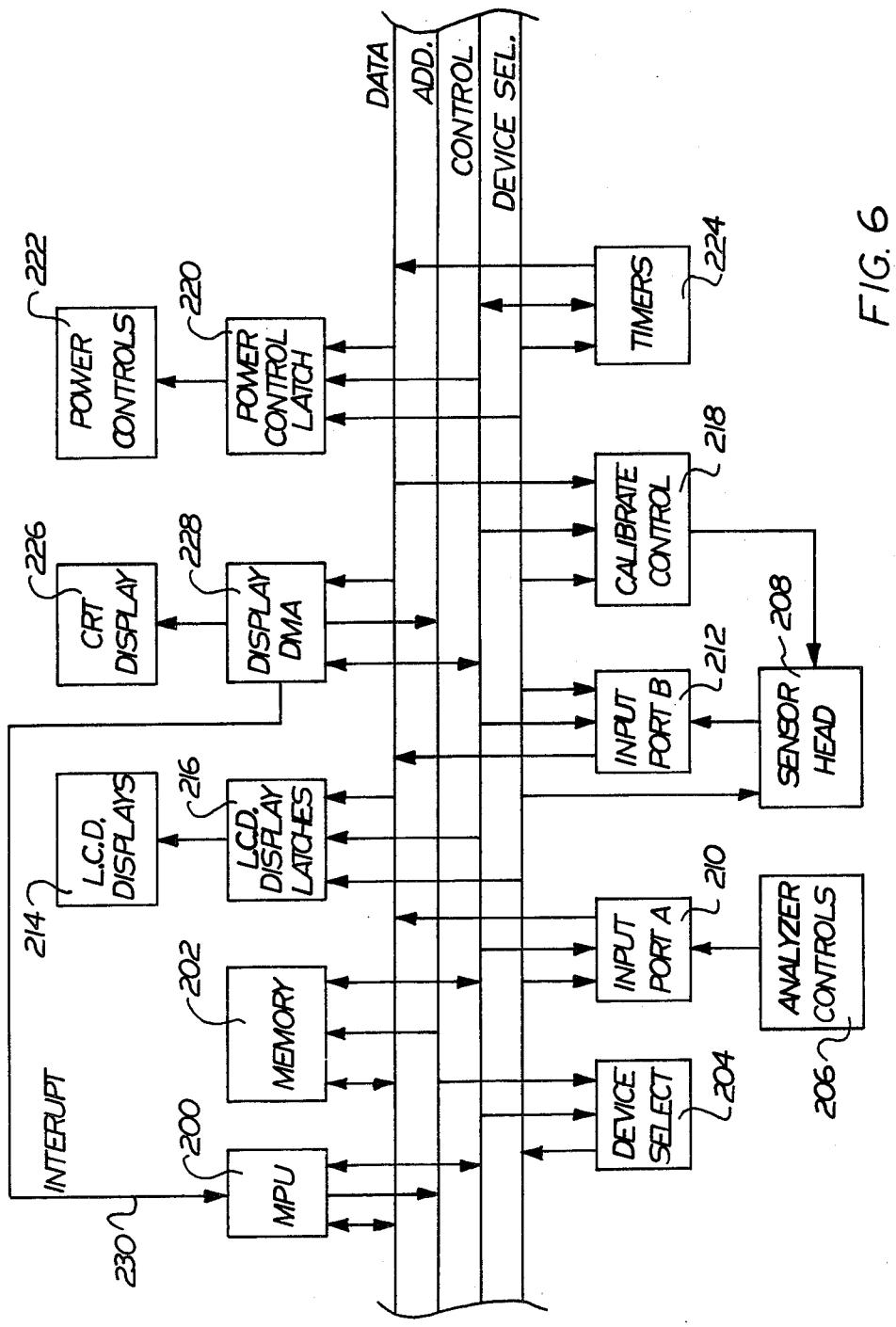
FIG. 6 is a broad block diagram of the control circuitry of the element analysis unit.

FIG. 6 broadly illustrates the electronics associated with the multi-channel analyzer and sensor head assembly of the X-ray fluorescent spectrometer. In this Figure it will be seen that a microprocessor 200 is provided to control the various operations of the X-ray fluorescent spectrometer. The various inputs and outputs of the system are connected to the microprocessor 200 by means of various buses. These buses include an eight bit wide data bus, a sixteen bit wide address bus, and a control bus. The instructions for operation of the microprocessor 200 are contained within a solid state memory 202, which will be comprised of several sections. One section of this memory will be comprised of read-only memory (ROM), and will contain the various control programs, and the permanent reference spectrums and look-up tables associated with the operation of the microprocessor 200. In addition, a section of random-access memory (RAM) will also be provided for storing spectrums of samples which have been analyzed previously, for providing storage of the various variable associated with the operation of the microprocessor 200, and for various other "scratch pad" purposes. This RAM will be continuously powered, independently of the power switch 18, so as to retain the stored data even when power is not being supplied to the remainder of the circuit.

The inputs and outputs of the system will be selected under control of device select commands provided by a device select decoder 204. This device select decoder 204 decodes the addresses provided by the microprocessor 200 to provide enabling signals to the input or output port or device which has been designated by the address on the address bus at that time. Thus, the device select decoder 204 provides plural output lines, each one of which will be directed to a corresponding input or output port or device. In FIG. 6, and hereinafter, these lines will be referred to as device select lines.

The inputs to the system are derived from two sources; the analyzer controls 206 which were described with respect to FIG. 2, and the sensor head 208 which was described with respect to FIGS. 4, 5 and 6. The analyzer controls are interfaced with the data bus by means of an input port 210, whereas the sensor head 208 is interfaced with the data bus by means of an input port 212.

The outputs from the system include the CRT display 226 and the LCD displays 214 provided on the face of the multi-channel analyzer, a calibrate control circuit 218, and a power control latch 220. The signals which are used to control the state of the LCD displays 214 are derived from display latches 216, associated therewith. The calibrate control circuit 218 includes programmable offset and gain control circuits, and is used to provide automatic calibration of the sensor head 208. The power control latch 220, on the other hand, is used to control the application of power to various high power dissipation elements within the circuit, and is controlled by the microprocessor 200 to disable the application of power to these elements in order to conserve power in various circumstances which will be described hereinafter.

A programmable interval timer 224 serves as another peripheral for the microprocessor 200, and includes a number of timers which are individually programmable by the microprocessor 200 to provide indications to the microprocessor when specific intervals have elapsed.

In addition to the foregoing, a cathode ray tube (CRT) display 226 is provided. Other display devices such as arrays of LED's or LCD's, for example, could of course be used in place of CRT 226, if desired. The CRT used in the described embodiment is controlled by a display DMA circuit 228 which will be described hereinafter. The display DMA controls the supply of the vertical and horizontal control signals, as well as the intensity signals to the CRT display 226, and operates somewhat independently of the microprocessor 200. During each individual scan of the CRT by the CRT display 226, the display DMA 228 operates to retrieve the necessary information from memory 202 without substantial disruption of the operation of the microprocessor 200. Upon the conclusion of each display scan, however, the display DMA 228 provides an interrupt signal along an interrupt line 230 to the microprocessor 200. This interrupt causes the microprocessor 200 to interrupt its programmed operation, and to shift instead to an interrupt procedure which is designed to service the display DMA and prepare it for the next succeeding scan. After this has been completed, the microprocessor 200 will return to the point in its regular programming at which it was interrupted.

Figure 7A:
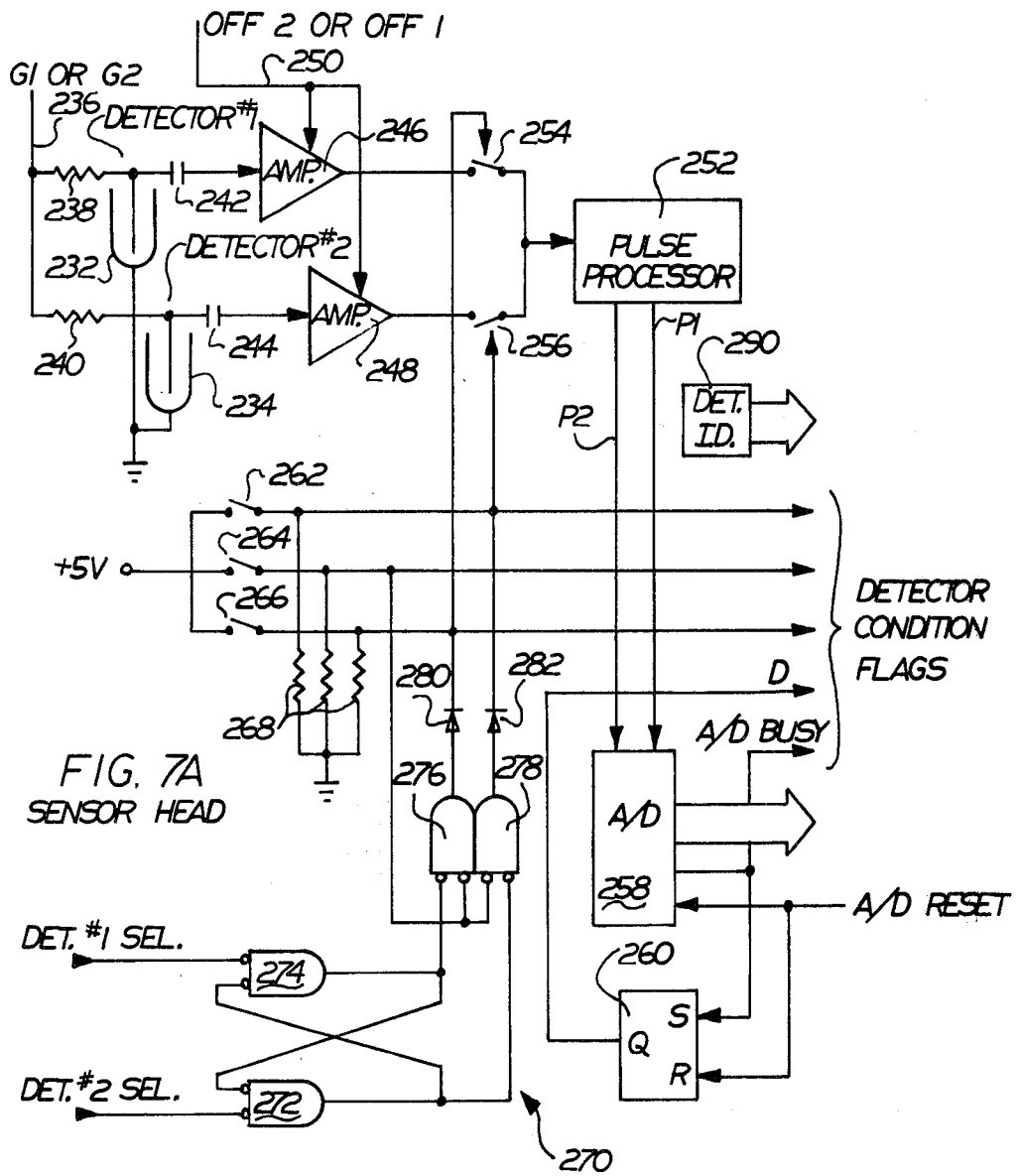
FIG. 7 is a more detailed illustration of the circuitry associated with the sensor head of FIG. 3.

FIG. 7A provides a more detailed illustration of the sensor head block 208 of FIG. 6. As shown in this figure, PC detectors 232 and 234 (corresponding to PC detectors 86, 90 of FIG. 3) each have one electrode connected to a high voltage line 236 through a respective isolation resistor 238 and 240, with the other electrode of each being connected to ground. The high voltage line 236 provides the necessary high voltage DC bias to each of the detectors 232 and 234 from the calibration control circuit 218 of FIG. 6. As stated previously, the X-ray fluorescent radiation emitted by the sample will produce brief deviations in the current across the detectors 232 and 234. In order to detect these current pulses, the outputs of the detectors are capacitor coupled via capacitors 242 and 244 to respective charge sensitive amplifiers 246 and 248. The capacitors 242 and 244 isolate the high potentials being applied to the electrodes of the PC detectors 232 and 234 from the amplifiers 246 and 248 while permitting the current pulses to be detected thereby. These amplifiers 246 and 248 are each further connected to a DC offset line 250 which is also derived from the calibration control circuit 218. The amplifiers essentially add the DC offset voltage on line 250 to the current pulses provided by the detectors.

A single pulse processor 252 is provided for processing the pulses appearing at the output of a selected one of amplifier 246 or 248. Two analog switches 254 and 256 (which will preferably be solid state FET switches) selectively connect either the output of amplifier 246 or the output of amplifier 248 to the input of pulse processor 252. Only one of analog switches 254 and 256 will be closed at any one time. The output of the pulse processor 252 will therefore reflect either the pulses provided by detector 232 or the pulses provided by detector 234.

Pulse processor 252 includes a peak detector circuit (not shown separately) which detects the peak amplitude of each pulse provided at the input to the pulse processor, and provides an analog signal on output P1 which has an amplitude proportional to this peak amplitude. Another circuit in the pulse processor provides a logic signal on output P2 which is normally at a low logic level, but switches high when peak amplitude information is available on output P1. The P2 output of pulse processor 252 is used to signal an analog-to-digital (A/D) converter 258 to begin conversion of the analog signal then on output P1 to a corresponding digital word. During that interval in which A/D converter 258 is busy with the conversion of a given analog signal to a corresponding digital word, an A/D BUSY line is raised to a high logic level. This high logic level sets an S/R flip-flop 260 to a high logic level, thus causing the output D thereof to also be raised to a high logic level. Although the A/D BUSY line will be returned to a low logic level upon the completion of conversion, the D line will remain at a high logic level until the flip-flop 26 is reset by a signal supplied by the microprocessor 200. The data word provided at the output of A/D converter 258, as well as the A/D BUSY line and the output D of flip-flop 260, are all provided to input port B in a manner which will described with respect to FIG. 8.

Also shown in FIG. 7 are the three microswitches 262, 264 and 266 associated with the shutter plate, and which indicate its position. Each of these microswitches is connected between a +5 voltage source on the one hand, and a corresponding pull-down resistor 268 on the other hand. The purpose of the pull-down resistors is to pull the voltage at the output of the respective switch down to a ground level when that switch is in an open state. The junction between the switches 262, 264 and 266 and the pull down resistors is provided to the microprocessor data bus via the input port B so as to indicate to the microprocessor the position of the shutter.

Switch 266 is associated with the position of the shutter plate wherein the opening 84 (FIG. 3) is exposed and the output of detector 86 is to be processed. It will be noted that the output of switch 266 is directly utilized to control the position of analog switch 254, so that the output of amplifier 246 will be connected to pulse processor 254 whenever switch 266 is depressed (indicating that detector 232 is to be active). Switch 266 is similarly utilized to directly control the position of analog switch 256, and will automatically connect detector 234 to the pulse processor 252 whenever that detector is to be used.

Switch 264 is normally open, and will be closed when the shutter plate is off of its center position. In addition to being used as an input to the microprocessor, the output of microswitch 264 is also used to enable circuitry 270 which is included to permit microprocessor selection of one or the other detector when the shutter is in its center position (i.e. when both calibration targets are in position over the openings in the sensor head). This logic circuitry 270 consists essentially of a flip-flop constructed of two cross-coupled AND gates with inverted inputs (more commonly referred to as NOR gates) 272 and 274. The two inputs to this flip-flop are derived from the microprocessor via the device select lines, so that the flip-flop may be set into either or its two states by the microprocessor.

The outputs of the flip-flop are used to control the positions of switches 254 and 256 when the switch 264 indicates that the shutter plate is at its center position. When the shutter plate is not at its center position, the control of the analog switches 254 and 256 by the flip-flop 270 is disabled by NOR gates 276 and 278. Thus, the outputs of NOR gates 276 and 278 will reflect the input provided by flip-flop 270 only when the switch 264 is in the illustrated position, i.e., when the shutter plate is at its center position. Two diodes 280 and 282 are used to isolate the outputs of switches 262 and 266 from the outputs of OR gates 276 and 278. If these diodes were not present, then the outputs of gates 276 and 278 would be directly connected to the +5 supply whenever one of switches 262 or 266 were closed.

As stated previously, a number of different sensor heads may be alternatively connected with the multi-channel analyzer, each having different types of detectors and radiation sources. In order to automatically indicate to the multi-channel analyzer which sensor head is being employed, a detector ID circuit 290 is utilized. This detector ID circuit 290 provides a three bit binary code identifying the detector. Since a three bit code is used, eight different sensor heads may be interchangeably employed with the multi-channel analyzer. Of course, if a larger number of sensor heads were available, then the ID circuit 290 would be expanded to provide a larger number of bits.

Figure 7B:
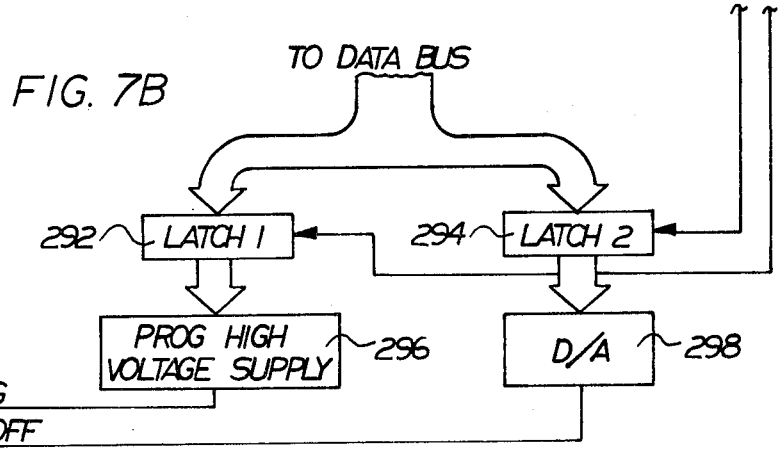

FIG. 7B illustrates the contents of the calibration control block 218 of FIG. 6 in greater detail. This calibration control circuit includes two latches 292 and 294, each of which is connected to the data bus. Two device select lines are used to actuate the latches 292 and 294 so as to clock appropriate data words into these latches. The output of latch 292 is used to provide digital word to a programmable high voltage supply circuit 296. This high voltage supply provides a controlled voltage to the high voltage line 236 in the sensor head 208. By controlling the digital word contained within latch 292, the voltage applied across the detectors, and thus their gain, can be controlled. The output of latch 294 is directly supplied to a digital-to-anlog (D/A) converter 298, where it is converted into a corresponding analog signal. This analog signal is used to provide the offset for amplifiers 246 and 248 within the sensor head circuitry of FIG. 7A.

It is, of course, highly unlikely that both of detectors 232 and 234 will require the same high voltage signal in order to properly adjust the gain of the multi-channel analyzer for that detector. It is similarly unlikely that the offset required by amplifiers 246 and 248 will be identical. It is therefore necessary to provide different digital words to the programmable high voltage supply 296 and the D/A converter 298, dependent upon which of the two detectors is to be utilized. As will be brought more fully hereinafter, the microprocessor provides the necessary data and device select signals to latch the appropriate digital words into latches 292 and 294 whenever the switches 262, 264 and 266 of the sensor head indicate that one or the other of the detectors 232 and 234 is to be enabled.

Figure 8:
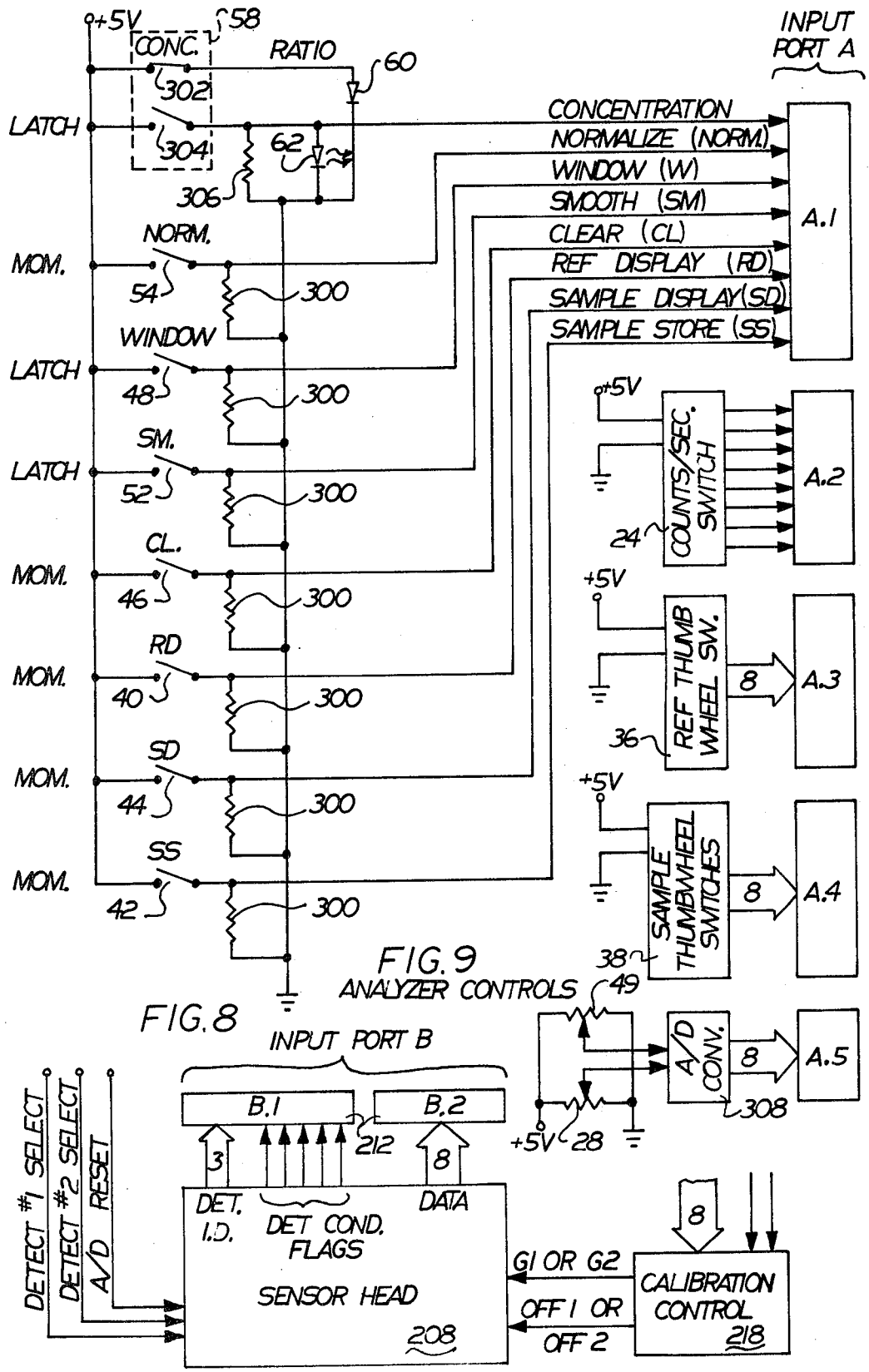
FIGS. 8A and 8B are block diagrams illustrating the manner of connection of the circuitry of FIG. 7 to the circuitry of FIG. 6.

FIG. 8 illustrates the manner in which the sensor head of FIG. 7A and the calibration control circuit of FIG. 7B are interconnected, as well as showing the manner in which the various signals are supplied to these two circuits from the remainder of the circuitry of FIG. 6. Input port B comprises two eight bit wide input ports B.1 and B.2. Input port B.1 is responsive to the various signals provided by the sensor head indicative of the detector condition, and to the three bit signal provided by the detector ID circuit 290. Input port B.2, on the other hand, responds to the eight bits of data provided by A/D converter 258, indicative of the amplitude (i.e. energy) of a particular pulse detected by one of detectors 232 and 234.

FIG. 9 illustrates in greater detail the analyzer controls, and their manner of interconnection with the microprocessor control system of FIG. 6. For convenience of description, the switches illustrated in FIG. 9 have been given the same reference number as the corresponding switches of FIG. 2. Each of switches 40, 42, 44, 46, 48, 52, and 54 is an SPST switch interconnected between a +5 V supply, and a corresponding pull-down resistor 300. As before, these pull-down resistors are included to pull the output of the switch down to a ground voltage level when the switch is in an open state. Preferably, switch 52 (which controls the SMOOTH function) and switch 48 (which controls the WINDOW function) will be latching switches which will latch into the open or closed position upon being depressed by the operator. Each of the remaining switches 40, 42, 44, 46, and 54 will, however, instead be momentary contact switches which will return to an open condition after being released by the operator.

The CONCENTRATION switch 58, unlike the other switches thus far described, is a latching DPDT switch having two poles 302 and 304. The normally open contact of pole 304 will be connected between the +5 V supply and a dropping resistor 306. An LED 62 including an internal dropping resistor is connected across the dropping resistor 306 so as to provide a visual indication of the status of the switch, and thus of the nature of the read-out provided along the LCD display 56 of FIG. 2. The other pole 302 of switch 58 is also connected between a +5 V supply and a second LED 60. Switch 302 is normally closed, whereas switch 304 will be normally open. Thus, at any given time +5 V will be supplied to one and only one of LEDs 60 and 62. These LED's therefore provide a visual indication of the state of the switch, and thus of the nature of the read out provided by the LCD displays 56 of FIG. 2.

The outputs of these eight switches are provided to one section of input port A, designated port A.1 in FIG. 9. Input port A also includes four other sections, to which are directed signals supplied by various other controls of the multi-channel analyzer. Thus, the counts/second switch 24 provides an eight bit word to input port A.2. The switch 24 is a single-pole eight-throw switch, and will provide a low voltage level to each of the eight outputs except one, which will be at a +5 V level. By rotating the switch 24, the one of the eight outputs which is at a high logic level may be shifted in one direction or the other. The thumb wheel switches 36 and 38 each provide eight bit words to the data bus via corresponding sections of input port A, sections A.3 and A.4.

The cursor potentiometer 28 and the window potentiometer 49 both provide variable analog signals to analog-to-digital (A/D) converter 308. A/D converter 308 converts one of these analog signals into a corresponding eight bit digital word and provides this digital word to a fifth section of the input port, designated A.5 in FIG. 9. The device select lines are used to select which analog signal is to be converted to digital.

The various sections of input port A thus serve to interface each of the controls provided on the face of the multi-channel analyzer with the data bus, except for the enhancement switch 50 which operates directly in conjunction with the display DMA circuit 228, shown more particularly in FIG. 10.

FIG. 10 illustrates in greater detail the circuitry utilized to display the spectrums upon the face of the video display screen 12, of FIG. 2. This display surface is preferably the face of a cathode ray tube (CRT) 310. CRT 310 is responsive to an X input and a Y input for positioning of an electron beam on the face thereof in a horizontal and vertical direction respectively. The CRT 310 is further responsive to a Z input for controlling the intensity of the electron beam as it scans across the face of the tube.

The scanning of the electron beam in the X direction across the face of the CRT is accomplished by providing the X input of CRT 310 with a ramp waveform supplied by X ramp generator 312. Ramp generator 312 provides at its output a voltage which increases linearly with time, and which is reset periodically by the microprocessor through use of one of the device select lines.

The displays provided by the CRT are generated by modulating the signal provided to the Y input thereof as the electron beam scans across the face of the tube in the X direction. This modulation is accomplished by sequentially reading out memory locations within a specific section of memory 202. The data which is to be displayed on the surface of display screen 12 will be stored in memory in the format shown in FIG. 11. Each energy channel will be assigned two 8-bit bytes within the memory. The first 8 bit byte will comprise the eight least significant bits of the number of counts which had been recorded for that channel. The second byte includes the six most significant bits of this count number, with the remaining two bits idenifying the desired intensity of the display.

Although the microprocessor could be used to read the data out of memory for display purposes, to do so would monopolize too great a portion of the microprocessor's time. A direct memory access (DMA) controller 314 is therefore provided to instead perform thus function. At the beginning of each scan of the screen 12 by CRT 310 (i.e. immediately following the resetting of X ramp generator 312 by the microprocessor), the microprocessor will load the DMA controller 314 with a selected initial memory address. DMA controller 314 will thereafter respond to clock pulses provided by a clock circuit 316 to sequentially read out the memory, from that initial address. The clocking rate of clocking circuit 316 is selected so the 128 clock cycles will transpire during the period of time in which the electron beam is scanning across the face of the CRT 310. DMA controller 314 treats the clock pulses generated by clock circuit 316 as DMA requests by the CRT. Consequently, with each clock pulse, the DMA controller 314 will provide a "hole" request to the microprocessor which will cause it to relinquish control of the data and address buses. After accomplishing this, the microprocessor will acknowledge the entry of a HOLD state to the DMA controller, indicating to the DMA controller that it may now directly access the memory through use of the data and addresses buses. DMA controller 314 will then sequentially provide two memory addresses along the address line, and will latch the data provided along the data bus by the memory in response to these addresses into the latch 318.

Fourteen of the 16 bits thus latched into latch 318, containing the number of counts for the energy channel then being displayed, are provided to a digital-to-analog converter 320, which converts them to a corresponding analog signal. This analog signal is provided to an amplifier 322 which has an antilogrithmic transfer characteristic. The output of the D/A converter 320 is also directly supplied to ENHANCEMENT switch 324, described earlier with respect to FIG. 1. When switch 324 is in one position, the output of D/A converter 320 is directly supplied to a vertical scale potentiometer 326. When the ENHANCEMENT switch is in the enhancement position, on the other hand, the output of the antilog amplifier 322 is instead supplied to the vertical scale potentiometer 326. When in this enhancement position, the vertical displacement along the display spectrum will be enhanced, due to the nonlinear transfer characteristics of antilog amplifier 322.

The vertical scale potentiometer 326 corresponds to potentiometer 68, described previously with respect to FIG. 1. The wiper arm of this potentiometer is connected to the Y input of the CRT 310. The gain of the spectrum 22 on the face of the video display screen 12 may be manually adjusted by appropriately changing the setting of the vertical scale potentiometer.

The two bits stored in latch 318 which correspond to the intensity control information are provided to an intensity control circuit, generally indicated at 328. The intensity control bits provided on output lines 344 and 346 are each used to implement a corresponding function. More specifically, the bit corresponding to the output line 344 is used to implement the "window" function, and will be referred to as the "window tag" hereinafter. The bit corresponding to output line 346 on the other hand, is used to define the cursors, and will thus be referred to as hereinafter as the "cursor tag".

The intensity of the electron beam on the face of the CRT will depend upon the impedence level of two analog switches 330 and 332 which respectively connect resistors 334 and 336 to a third resistor 338. When analog switch 330 is in a low impedence state, the voltage at the Z input into CRT 310 will depend upon the relative resistance values of resistors 334 and 338. When analog switch 330 is in a high impedence state, and analog switch 332 is instead in a low impedence state, the voltage level at the Z input to CRT 310 will instead depend upon the relative resistance values of resistors 336 and 338. When neither of analog switches 330 or 332 is in a low impedence state, however, the voltage level at the Z input to CRT 310 will be essentially at a ground level, and the CRT beam will be blanked.

The impedence levels of analog switches 332 and 330 are controlled by respective AND gates 340 and 342. When the output 344 of latch 318 is at a low impedence level, then both AND gates 340 and 342 will be disabled, resulting in both analog switches 330 and 332 being in high impedance states. Thus, whenever the voltage level at the output 344 of latch 318 is in a high logic level, the CRT 310 will be blanked. When the output 344 of latch 318 is at a high logic level, however, the output of AND gates 340 and 342 will instead depend upon the logic level at the second intensity control output 346 of latch 318. When this output is in a high logic level, then AND gate 342 and analog switch 330 will be enabled, resulting in a selected beam intensity on the face of the CRT 310. During this period, the output of AND gate 340 will be disabled since the output 346 of latch 318 is supplied thereto through an inverter 348. Similarly, when the output 346 of latch 318 is at a low logic level, AND gate 342 and analog switch 330 will be disabled, whereas AND gate 340 and analog switch 332 will be enabled. In this case, the intensity of the electron beam on the face of the CRT 310 will be at a different selected level. This permits display of a heightened-intensity cursor, as described previously.

As the electron beam scans across the face of the CRT 310, the clock 316 will trigger the DMA controller 314 to latch new intensity and Y deflection information into the latch 318 for each of the 128 channels which are to be displayed. After the conclusion of the display of all 128 channels, the DMA controller 314 will raise an interrupt flag along an interrupt line 350, connected to the interrupt input of the microprocessor 200, shown in FIG. 5. This interrupt will cause the microprocessor 200 to interrupt whatever procedure it was implementing at that time, and to service the display DMA to prepare for the next succeeding scan.

Figure 12:
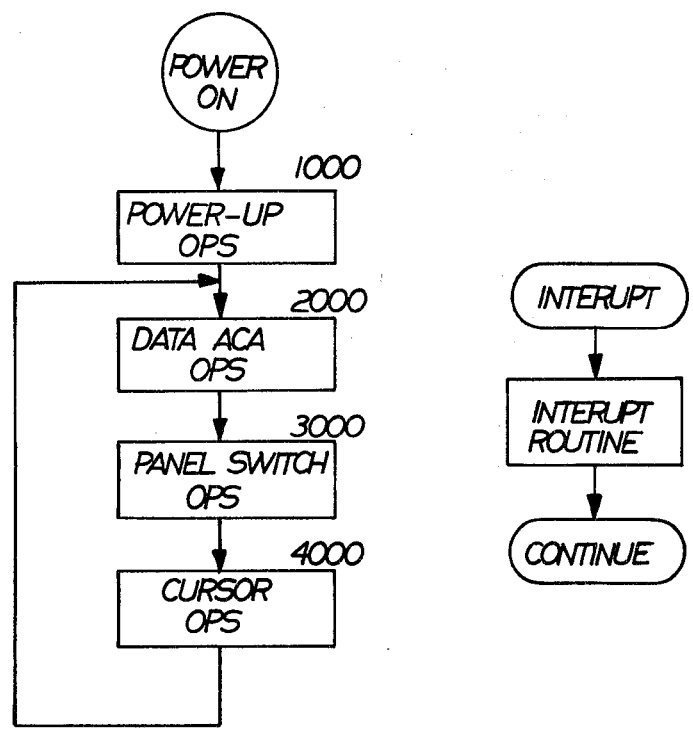
FIG. 12 is a broad flow chart illustrating the manner of operation of the circuitry of FIG. 6.
Figure 13:
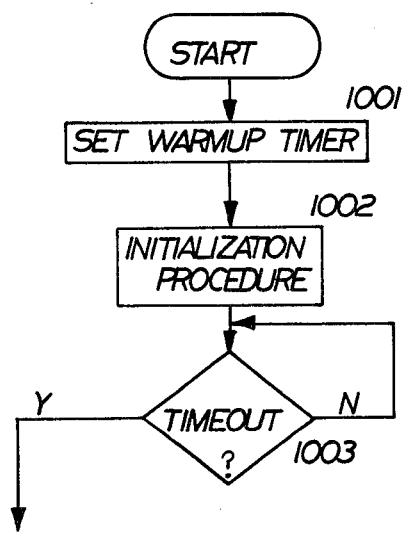
Figure 14:
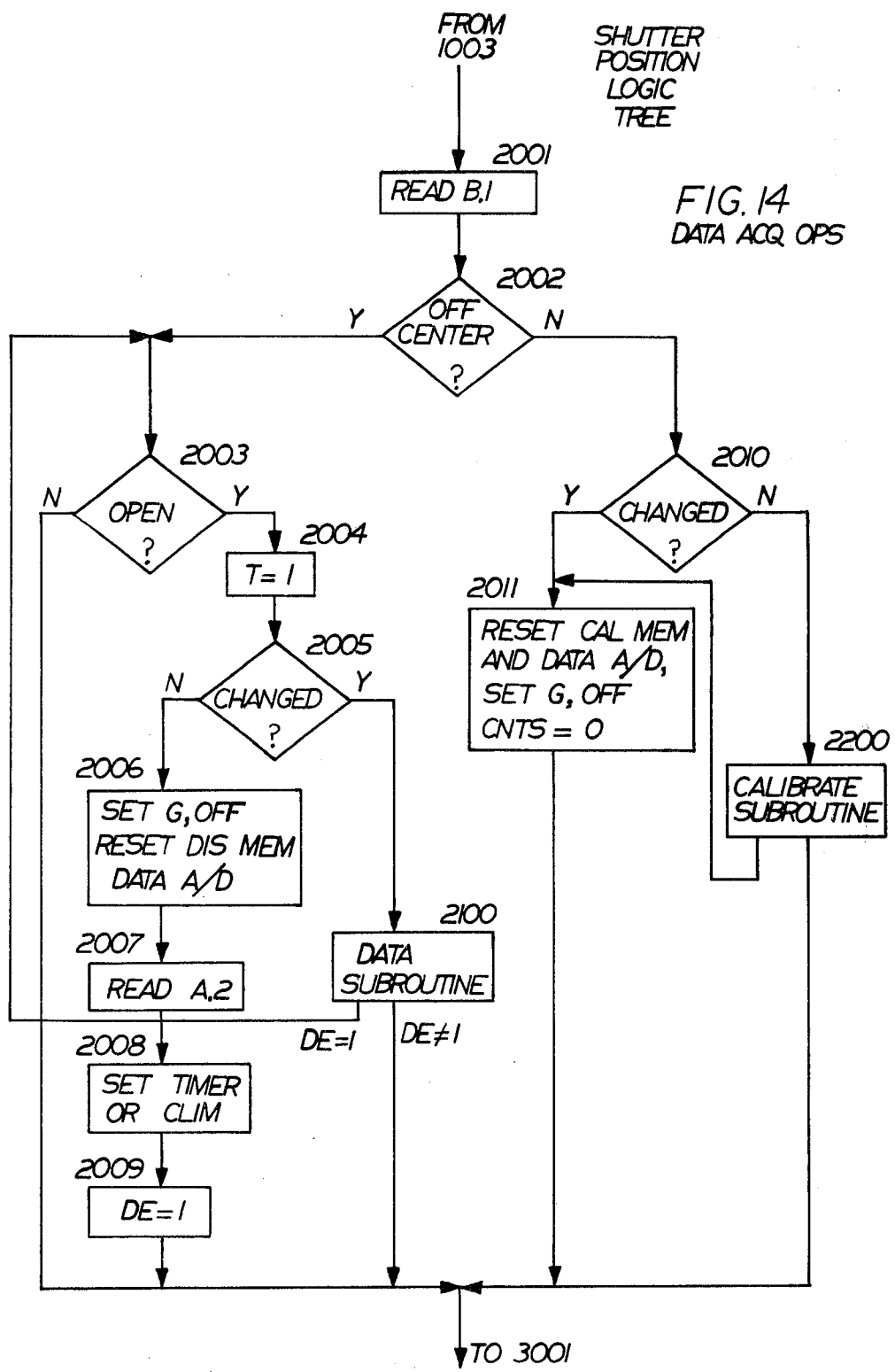
Figure 19:
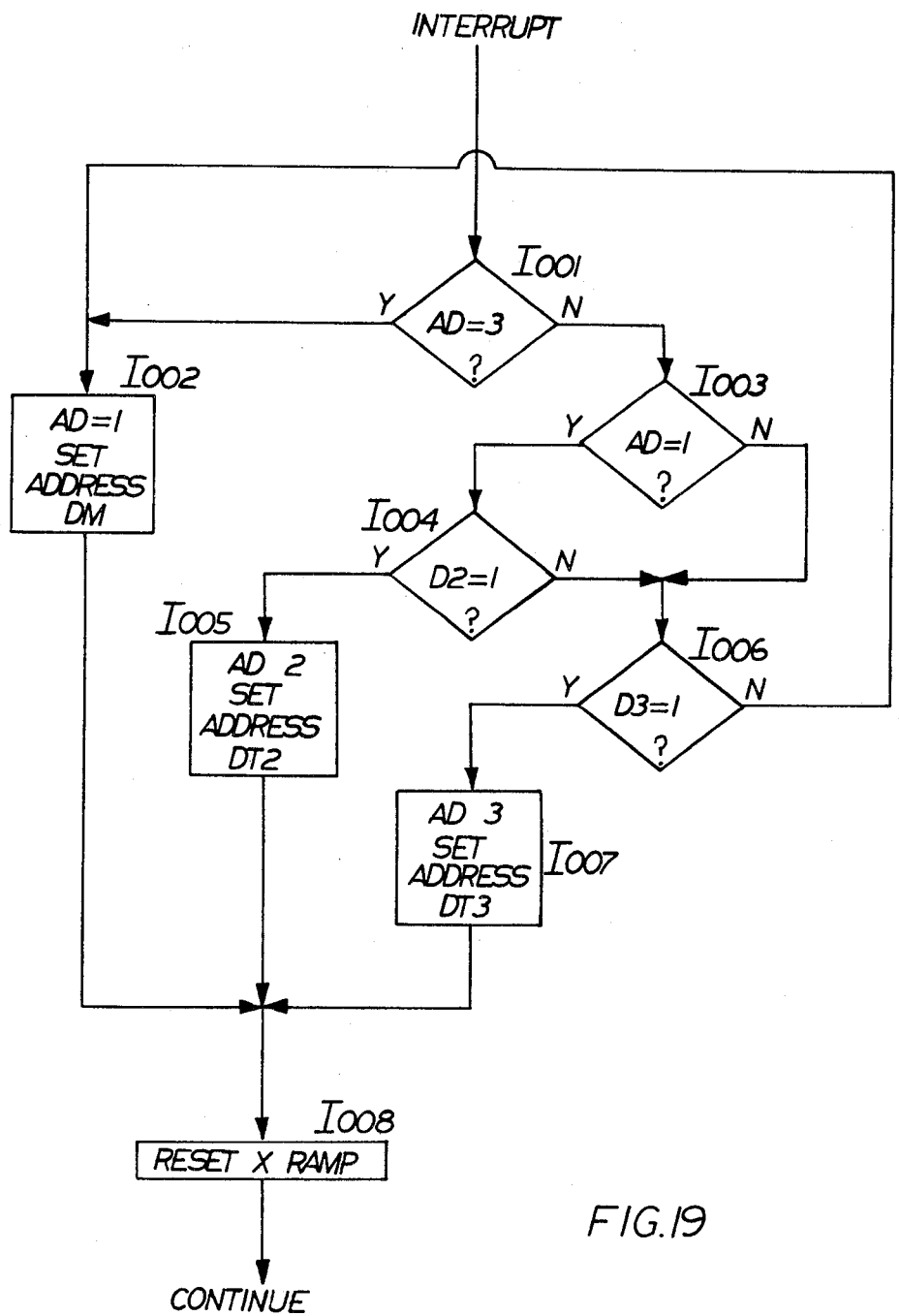

FIGS. 12–20 are flow charts detailing the sequence of operations performed by the microprocessor 200 under control of instructions loaded in the memory 202. FIG. 12 broadly illustrates the general structure of the programmed operation of microprocessor 200. When power is initially applied to the system, the microprocessor performs a series of power-up operation 1000. Upon completion of these power up operations, the microprocessor proceeds into the body of the program, where it specifically performs a series of operations, broadly separable into three different groups: data acquisition operations 2000, panel switch operation 3000, and cursor operations 4000.

The data acquisition operations 2000 generally include those operations necessary to acquire data from the sensor head. These operations thus include the sensing of the position of the shutter, calibration of the appropriate detector/amplifier assembly, as well as the actual acquisition of data. The panel switch operation 3000 generally include all of those functions performed under user control via the front panel switches, with the exception of those operations associated with the position of the cursor. The cursor operations 4000 separately deal with these cursor operations, including the sensing of the present setting of the cursor potentiometer 28, highlighting of the appropriate display positions on the display screen 12, etc.

The microprocessor will repetitively cycle through these three procedures 2000, 3000, and 4000 until either the power is turned off, or an interrupt request is received from the video display DMA 228 (FIG. 6). Upon receipt of an interrupt request, the microprocessor will store the contents of all internal registers within the microprocessor, and will jump to an interrupt routine which will instruct the microprocessor to perform the operations necessary to service the display DMA. This interrupt routine will be described in detail hereinafter. Upon the completion of the interrupt routine, the microprocessor will restore all internal registers to the condition they had been in upon receipt of the interrupt request, and will then proceed with the programmed performance of the procedures 2000, 3000 and 4000 from the point therein at which interruption had occurred.

A more detailed description will now be provided of each of these four procedures, as well as the interrupt routine. As used in the description which follows, a "cycle" is intended to refer to a single complete pass through procedures 2000, 3000, and 4000.

PROCEDURE 1000

Power-Up Operations

When power is initially applied to the microprocessor via the power switch 18 shown in FIG. 2, the microprocessor is automatically reset, and programmed operation begins at a predetermined address in the program memory therein. After resetting all integral registers and flags, the programmed operation proceeds to the beginning of the power-up operations, indicated in FIG. 12 as procedure 1000. This procedure generally includes all of those operations which must be performed by the microprocessor in order to initialize the system for normal operations. This procedure includes the following steps:

1001 This procedure sets one of the timers associated with timer 224 (FIG. 6) to a number corresponding to a time interval adequate to permit the analog circuitry contained within the sensor head to reach thermal equilibrium.

1002 As will be noted hereinafter, the microprocessor utilizes a number of counting variables in the execution of the various procedures, with the value of these counting variables being contained in specifically assigned locations in RAM. Others locations in RAM are used to store values indicative of the positions of the various front panel switches of the multichannel analyzer. This initialization procedure sets all of these counting variables to zero, and sets the switch variables at preprogrammed initial values. The initialization procedure also sets the value of various other variables utilized in the body of the program, e.g. the variables PD and T are set to "1" and CAL 1 and CAL 2 are set to "0". Finally, the initialization procedure sets the variables indicating the previous position of the shutter to "010" and sets the "not ready" light.

1003 In this step, the status of the timers is checked to determine whether or not the warm-up period has elapsed. If the warm up period has elapsed, the program flow continues to procedure 2000. If not, the step is repeated. The microprocessor thus cycles through step 1003 continuously, as long as the warm up timer has not timed out. Upon the conclusion of the warm up period, the timer status will change to indicate this fact, and the program flow will continue on to procedure 2000.

PROCEDURE 2000

Data Acquisition Operations

This procedure generally includes all of the functions required to sense the position of the shutter, to calibrate the sensor head, and to regulate the flow data from the sensor head. This procedure includes the following steps:

2001 In order to perform the data acquisition operation, it is necessary to determine the position of the shutter. In this step, the microprocessor reads input port B.1, thus reading the detector ID and the detector condition flags.

2002 If the detector condition flags indicate that the shutter is on center, the program flow jumps to step 2010. Otherwise, the program flow continues on to step 2003.

2003 If the shutter, although off center, is not fully open, the program jumps to the panel switch operations 3000. If thr detector condition flags indicate that the shutter is in a fully open position, however, the procedure continues on to step 2004.

2004 As indicated previously, the failure of the operator to perform a manual function within a certain time interval will result in the element analysis unit reverting to a "power down" state in which various high power dissipation elements of the system are de-energized to save power. A variable "T" is used in order to indicate whether or not the operator has performed the manual function within a predetermined time interval. In this step, the variable T is set equal to a binary value of "1", thus indicating that the operator has performed a manual operation (in this case, shutter actuation) during this cycle.

2005 The microprocessor checks the stored indication from the previous cycle as to whether or not the shutter was open during that previous cycle. If the shutter was, in fact, also open during the previous cycle, the program jumps to step 2100. Otherwise, the program continues on to step 2006.

2006 The purpose of this step is to initialize the data storage memory (display memory) and certain other factors when the shutter is first opened. The gain and offset for the selected shutter are read out from memory into latches 262 and 264 (FIG. 7B) associated with the calibration control circuit 218 of FIG. 6. By the time the microprocessor reaches this step, these gain and offset values will have been calculated during a calibration subroutine 2200, to be described hereinafter. Also during this procedure, the microprocessor loads zero values into the memory location corresponding to the 128 counters which keep track of the number of counts in each energy channel. This initializes these counters (which will be referred to hereinafter as the display memory, or DIS MEM) in preparation for the receipt of data. Finally, the microprocessor addresses the device select circuit 204 to produce a signal select signal along the A/D reset line, thereby resetting the A/D converter 258 and flip-flop 260 of FIG. 7A.

2007 The input port A.2 is read in order to determine the setting of the second/count switch 24.

2008 If the byte read from input port A.2 indicates that a count mode has been set, the initial value of a variable CLIM will be set to the number identified by the position of the switch 24. If a timer mode was, however, instead selected, the microprocessor 200 will instead set one of the timers associated with the timer circuit 224 to time out after a time interval corresponding to the time selected by the position of the switch 24.

2009 The "data enable" variable DE is set to a binary "1" value, thuse enabling the taking of data by the microprocessor. The program then jumps on to procedure 3000.

2010 In the event that the shutter is on center, as it should be when power is first applied, the microprocessor performs a calibration routine, beginning with this step. If the stored indication as to the shutter position on the previous cycle indicates that the shutter was on center in the previous cycle as well, the program jumps to the calibration subroutine 2200. Otherwise, program flow continues on to step 2011.

2011 When the shutter first arrives at the center position, the program will pass through this step. During this step, the microprocessor will load a zero value into each memory location corresponding to the 128 counters associated with a "calibration memory". This calibration memory (or CAL MEM) is similar to, but distinct from the display memory, and permits the accumulation of a calibration spectrum therein while the data spectrum stored in the display memory is being displayed on the CRT. During this step, the microprocessor will also reset the data A/D, and set CNTS to 0. Also, the calibrate control circuit 218 is loaded with the presently stored values of G and OFF corresponding to the detector being selected by circuit 270. The program then jumps to procedure 3000.

The procedures 2100 and 2200 are data handling subroutines whose purpose is to load the data acquired from the sensor head into the display memory, or the calibrate memory. These subroutines will now be separately described with reference to FIGS. 15 and 16.

Procedure 2100

Data Subroutine

When the operator initially applies power to the system, the system will proceed through the power up routine, and then, presuming that the shutter has not been operated, will proceed through the calibration subroutine. The calibration subroutine, described in detail hereinafter, sets the gain and offset values for the two detectors in the sensor head, and then extinguishes the "not ready" light on the face of the element analysis unit. At this point, the operator is free to begin taking data by opening the shutter. When the shutter is first opened, the microprocessor will proceed through steps 2006-2009, thus preparing the element analysis unit for the taking of the new set of data. In the next cycle, however, program flow will instead shift to the data subroutine 2100 via step 2010. The program flow will jump back to the step 2003 after each pass through the data subroutine until the variable DE has a value of 1, indicating that a complete spectrum has been acquired, or the shutter is closed. The data subroutine includes the following steps:

2101 If the data enable variable (DE) has a logic value of 1, indicating that data is to be taken, program flow continues on to step 2102. Otherwise, the program jumps out of the data subroutine and on to procedure 3000.

2102 The input port B.1 is read, in order to determine whether or not data is available at the port B.2. If the data signal D, read from port B.1, has a logic value of 1, then data is available for processing. In this event, the program proceeds on to step 2103. Otherwise, the program loops back to step 2003.

2103 If the A/D busy line, also read via gate B.1, indicates that the data A/D is still busy with the conversion of the data signal to a digital value, the program again jumps out of the data subroutine and back to step 2003. If the data A/D busy line indicates that conversion of the signal to a corresponding digital signal has been completed, the program continues with step 2104.

2104 The microprocessor performs three functions in this step. (a) It reads the data from the A/D converter 258 of the sensor head via the input port B.2. (b) The microprocessor increments by 2 the number contained in the channel of the display memory which is identified by the value of the data read from the port B.2. If the stored variable associated with the smoothing switch 52 indicates that this function has been activated by the operator, the microprocessor also increments by one the numbers in the two channels adjacent to the one addressed by the data byte from port B.2. This has the effect of minimizing statistical variations in the spectrum, as acquired. Of course, other smoothing functions could also be employed. (c) The microprocessor resets the A/D and D lines via the device select circuit 204.

2105 If the "counts" mode has been selected via the switch 24 (FIG. 2) the program continues on to step 2106. Otherwise, the program shifts to step 2109.

2106 The counts variable CNTS, which maintains a running count of the number of data points which have been stored in the display memory, is incremented by 1.

2107 A variable CLIM, selected in accordance with the position of switch 24 to have a value of 250, 1K, 16K, or 64K, indicates the number of counts which are to be accumulated to assembly the sample spectrum. In this step, the present CNTS value is compared with the CLIM to determine whether or not the proper number of counts have been recorded yet. If the count has reached the limit, the program jumps on to step 2111. Otherwise, the program continues on to step 2108.

2108 The present value of the CNTS variable is read out to the alphanumeric display 26, and the program then again loops back to step 2003.

2109 If the element analysis unit is being operated in a fixed time interval mode, the microprocessor will at this time read the status of the timer 224 to determine whether or not this time interval has elapsed. If the timer interval has not as yet elapsed, the program continues on to step 2110. Otherwise, the program will jump to step 2111.

2110 The elapsed time is readout to display 26, and program flow again loops back to step 2003.

2111 When either the number of counts has reached the set limit or the timed interval has elapsed, the data enable (DE) variable is set to a logic value of 0. This prohibits the taking of further data in succeeding cycles by causing the program control to jump out of the data subroutine at step 2101.

Procedure 2200

Calibrate Subroutine

The calibrate subroutine is performed whenever the shutter is in a fully closed (on center) position. When the shutter first arrives at the fully closed position, the analysis unit is prepared for the calibrate subroutine by step 2011. Thereafter, the calibrate subroutine essentially accumulates data for a predetermined number of counts, determines the peaks in the calibration spectrum thus derived, and then compares the position of these peaks to the position which the peaks would have if the unit were properly calibrated. Any difference between the actual and desired location of the peaks will be adjusted out by resetting the gain and offset signals. Whenever the unit is not fully calibrated, the "not ready" light 20 on the front panel of the element analysis unit will be illuminated. When the unit is fully calibrated, of course, the "not ready" light will be extinguished.

2201 If the variable D, read from port B.1, has a binary value of 1, then a data pulse is available at the sensor head and the program continues with step 2202. Otherwise, (i.e. if no data is yet available) the program jumps out of the calibrate subroutine and on to procedure 3000.

2202 If the data A/D is still busy with the conversion of the analog data signal to a corresponding binary word, then, again, the program jumps out of the calibrate subroutine and on to procedure 3000. Otherwise, the program continues with step 2203.

2203 The microprocessor performs four different operations in this step. (a) The input port B.2 is read. (b) The numbers stored in the location in the calibration memory which is identified by the data word read from the input port B.2 is incremented by one. (c) The CNT variable is incremented by one. (d) The A-D converter 258 and flip-flop 260 (FIG. 7A) are reset via the device select line.

2204 The present value of the CNT variable is compared with a stored limit A. If the maximum count A has not yet been reached, the program jumps out of the calibration subroutine, and on to procedure 3000. In the event that the CNT count is equal to the maximum count limit A, program flow continues on to step 2205.

2205 The microprocessor performs three operations in this step. (a) The microprocessor examines the calibration spectrum which has been accumulated within the calibration memory and determines the two channels P1 and P2 representing the peaks of the calibration spectrum. (b) The channel numbers SET1 and SET2 defining the desired position of the peaks is read from memory, in accordance with the detector ID read from the ID circuit 290 associated with the sensor head, and the detector condition flags which indicate which of the two detectors has been utilized to provide the calibration spectrum. (c) The microprocessor compares the actual values of the peaks (P1, P2) with the desired values (SET1, SET2) and from the relative values of these variables determines the extent to which the gain and offset signals must be changed to correct for differences therein.

2206 The amount by which the gain and offset signals must be changed is compared with preset tolerances to determine whether or not a change in the actual gain and offset values must be made. If the gain and offset are accurately set to within the required tolerance, the program flow continues on to step 2207. Otherwise, the program flow jumps to step 2208.

2207 Since it has been determined that the detector which was used to accumulate the calibration spectrum was calibrated to within the correct tolerance, the variable CAL1 or CAL2 corresponding to that detector is set to a binary value of 1, thus indicating that that detector has been calibrated. In addition, the detector select lines are used to change the state of the flip-flop 270 of FIG. 7A, so that the next detector is selected for calibration.

2208 In the event that the gain and offset are not correct within the tolerance values, this step updates the gain and offset control signals which are stored in memory in accordance with the incremental changes necessary to bring them within tolerance. These values are then read out to the latches 292 and 294 associated with the calibration control circuit 218, as shown in FIG. 7B. The calibration variable associated with that detector (i.e. either CAL1 or CAL2) is then set to 0, indicating that that detector is not calibrated. The program then proceeds on to step 2209.

2209 If both calibration flags (i.e., CAL1 and CAL2) have values of 1, then the entire unit is properly calibrated. In this event, the program flow continues on to step 2210. Otherwise, the program flow jumps to step 2211.

2210 The "not ready" light is extinguished, thus signaling the operator that the unit is properly calibrated. The program flow then jumps to step 2011.

2211 The "not ready" light is turned on to signal the operator that at least one of the detectors has not as yet been calibrated. Again, program flow then jumps to step 2011.

Procedure 3000

Panel Switch Operation

In this procedure, the microprocessor checks the positions of the various switches associated with the front panel of the unit, and performs the operations necessary to implement the functions requested thereby.

3001 The microprocessor reads the position of the panel switches by reading the input port A.1. The byte read from input port A.1 is comprised of eight bits, each representing the position of a corresponding switch on the front panel of the element analysis unit. These bits will hereinafter be referred by the abbreviations shown in FIG. 9 adjacent to the input port A.1. Thus, for example, the clear bit will be designated as bit CL, whereas the smooth bit will be designated by the abbreviation SM.

3002 The byte indicating the present position of the switches is compared with a stored byte representing the previous position of the switches. If the results of this comparison indicate that the position of the switches has not changed, the program flow jumps to step 3016. If, however, one or more of the switch positions has changed, the program flow continues on to step 3003.

3003 As stated earlier, the microprocessor incorporates a power down function which will operate to turn off various high power dissipation elements of the unit when no manual operation has been performed within a selected time interval. In order to determine, in each cycle, whether a manual operation has been performed which will reset the power down timer, a variable T is used. In this step, the variable T is set to have a binary value of 1, indicating that a manual operation has been performed during this operational cycle. This variable T is used later on in the program, in steps 3016–3020.

3004 One of the bits (designated hereinafter as bit SS) read from the input port A.1 indicates whether or not the SAMPLE STORE button 42 on the front panel of the element analysis unit has been depressed by the operator. If this button has been depressed, the program continues on with step 3005. Otherwise, step 3005 is bypassed and the program flow continues at step 3006.

3005 Two functions are performed in this step. (a) A byte SA is read from the input port A.4. This byte, derived from the thumbwheel switches 38, designates the location in memory at which an accumulated data spectrum is to be stored. (b) The microprocessor operates to copy the data contained within the display memory at the position in memory designated by the byte SA. The data continued within the display memory is thus stored for later use, and may be recalled at any time by the pressing of the SD button 44.

3006 If the bit CL has a binary value of 1, indicating that the clear button 46 has been depressed to clear the second and third traces from the display, then the program flow continues to step 3007. Otherwise, step 3007 is skipped and the program flow continues with 3008.

3007 The value of the variables D2 and D3 are set equal to 0. This changes the operation of the interrupt routine through a logic tree which will be described hereinafter, and eliminates any second and third traces which may have been displayed upon the display screen.

3008 If the NORM bit has a logic value of "1", indicating that the normalization button has been depressed and that the display is to be normalized, the program continues on to step 3009. Otherwise, this step is bypassed, and the program continues at step 3010.

3009 Two operations are performed in this step (a) A channel number is recalled from memory designating the channel number at which the backscatter peak (BP) should occur for the detector/source combination then being used. The number of counts accumulated in a selected number of channels (e.g. seven) of the display memory centered on the BP channel are then read, and added together. The sum signal thus derived corresponds generally to the integral of the backscatter peak. (b) The contents of the display memory are then normalized by dividing the count contained within each channel by a value proportional to this sum signal.

3010 If the bit RD has a logic value of "1", indicating that the RD button 40 on the front panel of the unit has been depressed so as to call a reference spectrum from memory, then the program continues with step 3011. Otherwise, this step is bypassed and program flow continues at step 3012.

3011 Two operations are performed in this step. (a) The value of the variable D2 is set to a binary value of "1" if it was previously "0". This changes the operation of the interrupt routine so as to cause a second trace (i.e. the reference spectrum) to be displayed. If the variable D2 already had a value of "1", however, it is now changed to "0". This causes the removal of the second trace from the screen. The operator can thus add or delete the reference spectrum by depressing the reference display buttom 40. (b) A variable comprising an entire byte, and referred to hereinafter as DT2, is set to have a value corresponding to the byte read from input port A.3. This value identifies the starting address of the data block in memory containing the data for producing the reference spectrum which is to be displayed.

3012 If the bit SD has a logic value of "1", indicating that the SD button 44 has been depressed so as to call a previously stored data spectrum from memory, then the program continues with step 3013. Otherwise, this step is bypassed and program flow continues at step 3014.

3013 Two operations are again performed in this step. (a) The value of the variable D3 is set to "1" if it was previously at a value of "0". This changes the operation of the interrupt routine so as to cause a third trace to be displayed. If the variable D3 already had a value of "1", however, it is now changed to "0". This causes the removal of the second trace from the screen. The operator can thus add or delete the sample spectrum by depressing the sample display button 44. (b) A variable comprising an entire bit, referred to hereinafter as DT3 is set to have a value corresponding to the byte read from input port A.4. This value identifies the starting address of the data block in memory containing the data for the display of the third trace.

3014 If the logic signal W, derived from the window switch 48, has changed, or if the setting of the window potentiometer 49 has changed, then the program flow continues on with step 3015. Otherwise, the program jumps to step 3016.

3015 The variable bit WN is set to have a value of "1". This indicates to a procedure described hereinafter that the window tags of each channel in the display memory must be revised in accordance with the new position of the window controls 48 and 49.

3016 It will be recalled that the variable T indicates whether or not the operator has performed an operation with the element analysis unit during the preceding cycle. In the event that this variable has a logic value of "1", the power down timer must be reset. This is accomplished by jumping to step 3020, if T is equal to 1. If T is not equal to one, however, program flow continues on with the branch including steps 3017, 3018, and 3019.

3017 Since no manual operations have been performed in this cycle, the powerdown timer is not reset. Instead, the micrprocessor reads the status of the timers 224 to determine whether or not the power down timer has completed the timing of the interval.

3018 If the information read from the timers 224 indicates that the power down timer has completed the timing of the interval, then the program continues with step 3019. Otherwise, program flow continues on to procedure 4000.

3019 Since the power down timer indicates that the powerdown time interval has elapsed, the variable PD is set equal to 1. This value is then read out to the power control latch 220, which will cause the power control 222 to disconnect high dissipation elements of the element analysis unit from the power supply.

3020 If it was determined in step 3016 that the variable T had a logic value of "1", this step would cause the microprocessor to set the variable TD to "0", and to read out this value to the power control latch 220. If the element analysis unit had been in a power down status, this will cause all systems in the unit to again be brought up to power. It will be noted that T will have a value of "1" whenever any of switches 40, 42, 44, 46, 48, 52, 54 or 58 has been changed or the cursor is moved. The timing variable T will also have a value of "1" if the shutter has been opened during this interval. In this step, the microprocessor also resets the timing variables T to a value of "0" to prepare for the next succeeding cycle, and resets the power down timer in the timer peripheral 224. Program flow then continues with procedure 4000.

Procedure 4000

Cursor Operations

In this procedure, the microprocessor reads the position of the cursor, and performs all cursor related tasks. These tasks includes the repositioning of the visual cursor on the display of the display screen 12, as well as the generation of the secondary peak indications referred to previously. Furthermore, this procedure includes a step for repositioning the WINDOW on the new cursor position whenever the WINDOW button is latched and the cursor is moved, and of revising the width of the window in accordance with the setting of window potentiometer 49. This procedure also includes a step for determining the ratio of the height of the spectrum at the position at which the cursor is located, with respect to the height of the spectrum in the channel corresponding to the backscatter peak for the particular detector being employed. In the event that the CONCENTRATION button has been latched, this procedure then goes on to look up the concentration of the selected element in accordance with the ratio determined. This procedure includes the following steps:

4001 The input port A.5 is read so as to determine the present position of the cursor potentiometer. The variable NC is set to this value.

4002 The present position of the cursor, as indicated by the variable NC, is compared with the position which the cursor occupied in the previous cycle, as indicated by a variable OC. If these two variables have the same value, indicating that the cursor potentiometer has not been moved, then the program jumps to step 4004. If the two variables do not have the same value, however, then program continues with step 4003.

4003 Five different functions are performed in this step. (a) The two intensity bits (i.e. both the window and cursor tags) of each of the 128 channels of the display memory are reset to have a value of 01. This essentially eliminates the window function, and removes all highlighting for both the cursor and secondary peak indications from the display. (b) The variables WN, and T are set to have a binary value of 1, thus indicating to a later step in the program that the window tags must be reset. (c) The variable OC is set to have a value corresponding to the present value of NC, so that OC now indicates the present position of the cursor. (d) The cursor tags in the display memory are revised so as to highlight the display in those channels corresponding to the present position of the cursor, as indicated by the variable OC, and the secondary peaks. The memory includes a look-up table for each detector, each table including a list of the channels associated with the secondary peaks for each position of the cursor. By using the detector I.D. and detector condition flags to select the proper table and using the variable OC to reference this table, the channel numbers at which the secondary peak indications are to be located is determined. The microprocessor then loads the cursor tags of these channels with a value of "1" so that these channels will be highlighted in the display, thus indicating the presence of the secondary peaks. The microprocessor also sets the cursor tag in the channel identified by the variable OC, so as to highlight the channel corresponding to the cursor channel. (e) The variable OC is also used to index another look up table (also selected by the detector I.D. and detector condition flags), this one containing data for generating a display of the element symbol and channel number for the present position of the cursor. The data thus obtained is read out to the LCD display latches 216, and thus to the LCD displays 32 and 30 on the control panel of the element analysis unit.

4004 If the variable WN has a value of "1", and the variable W has a value of "1", then new window tags must be loaded into the intensity control portion of each of the channels of the display memory, and program flow continues with step 4005. If either of these variables (WN or W) has a value of "0", however, then the window tags will remain unchanged, and the program will jump to step 4006.

4005 Three functions are performed in this step. (a) The setting of the window potentiometer is read from input port A.5. (b) New window tags are loaded into the 128 channels of the display memory, in accordance with the present position of the cursor as identified by the variable OC. Essentially, all of the window tags will be set to a value of 0, except for the window tags associated with the channels which are within a selected number of channels of the present position of the cursor, as identified by variable OC. The number of channels on either side of the cursor which are loaded with window tags of "1" is directly related to the value of the digital word read from port A.5. This effectively blanks the entire spectrum 22 on display screen 12, except for that portion centering on the present position of the cursor. (c) The variable WN is reset to have a value of "0". Because of (c), step 4005 will be bypassed in succeeding cycles, unless the cursor position or window width has been changed. If the cursor position has been changed, then the variable WN will be given a value of "1" through the operation of step 4003, and the position of the window will be revised accordingly.

4006 In order to permit the operator to distinguish visually between the cursor and the secondary peak indications, the highlighting of the cursor is periodically eliminated, so that it "blinks". The timing of this blinking is controlled by one of the timers (referred to hereinafter as the blink timer) within the timer peripheral 224 (FIG. 6). In this step the status of the blink timer is read.

4007 If the blank timer has timed-out, program flow continues with step 4008. If not, step 4008 is bypassed, and the program continues directly to step 4009.

4008 Two functions are performed in this step. (a) The cursor tag associated with channel OC is changed from whatever state it previously had, into the alternative state. Thus, if it previously had a value of "1", it will be switched to have a value of "0" instead. Conversely, if it had a value of "0" already, then it will be switched to have a binary value of "1". Thus, with succeeding time-outs, the cursor tag will be shifted back and forth between binary values of "1" and "0". This will produce the blinking effect described previously. (b) The blink timer will then be reset.

4009 Again, two functions are performed in this step. (a) The ratio of count in the cursor channel is divided by the number of counts in the backscatter (BP) channel, so as to thereby provide a determination of the ratio of the number of counts in these two channels. (b) This ratio number is then used to index one of a number of stored look-up tables. The look-up table used is selected upon the basis of the detector ID, the actual detector selector, the present cursor position, and the present position of the reference thumbwheel switches 36. Thus, the cursor position indicates which element a concentration figure is desired for, whereas the remaining values indicate the type of mineral being analyzed. In order to improve the integrity of the concentration determination, the operator should first set the reference thumbwheel switches 36 to call the reference spectrum most nearly corresponding in form to the sample spectrum. Each of these look-up tables will essentially represent a cross correlation between the ratio value, and a concentration value for a particular element in a particular mineral. Consequently, by applying the ratio number to the particular look up table selected, a concentration figure may be derived.

4010 If the variable CONC has a binary value of "1" indicating that the CONCENTRATION button has been depressed, then the program will jump to step 4012. Otherwise, program flow will continue with step 4011.

4011 When the CONCENTRATION button has not been depressed, the ratio value will be read out to and displayed in the LCD display 56. The program will then jump back to step 2001 to begin a new operational cycle.

4012 If the CONCENTRATION button has been depressed, the concentration which was determined in step 4009 will instead be read out to and displayed in LCD displays 56. Again, the program will then jump back to step 2001.

Interrupt Routine

The interrupt routine is called whenever the display DMA completes the reading of all 128 channels of a spectrum for a given scan. When the interrupt signal is provided to the microprocessor 200, the microprocessor will store the present contents of all internal registers and flags in locations in the memory 202, and will then jump to an interrupt routine which will now be described. The purpose of this interrupt routine is to determine which starting address to load into the display DMA 228. The address which will be thus loaded into the display DMA will identify the first channel which is to be displayed upon the surface of the CRT screen 12. The display DMA will then increment sequentially from this location to display each of the remaining 127 channels. The three starting addresses which are available for supply to the display DMA correspond to the display memory, the reference memory which was identified by the position of the thumbwheel switches 36 at the time when the display button 40 was depressed, and the sample memory which was identified by the position of sample thumbwheel switches 38 at the time when the display button 44 was depressed. If neither of buttons 40 or 44 has been depressed, then the interrupt routine will only load the starting address of the display memory into the display DMA. The variable AD, utilized in the logic which will be described hereinafter, is a counting variable whose purpose is to identify which of the three spectrums was last displayed upon the display screen 12. The interrupt routine determines which starting address to next load into the display DMA upon the basis of the value of this variable. The interrupt routine includes the following steps:

I001 If the counting variable AD has a value of 3, then program flow continues on with step I002. Otherwise, the program jumps to step I003.

I002 The counting variable AD is reset to have a value of 1, and the display DMA is loaded with a starting address representing the starting address of the display memory. The program then jumps to step I008.

I003 If the counting variable AD has a value of 1, the program flow continues with step I004. Otherwise, the program jumps to step I006.

I004 If the variable D2 has a value of 1, then the operator has elected to display a sample spectrum stored in the sample memory, and this display must be provided next (see steps 3010, 3011). Program flow will thus continue with step I005. Otherwise, the program flow will jump to step I006.

I005 The variable AD is set to have a value of 2, and the display DMA is loaded with the starting address of the sample memory which was identified by the position of thumbwheel switches 38 when the display button 44 was depressed by the operator. The program then jumps to step I008.

I006 If the variable D3 has a value of 1, the operator has elected to display a reference spectrum stored within memory (see steps 3012, 3013). The program flow will thus continue with step I007. If the variable D3 has a value of 0, however, the program will jump to step I002, and the contents of the display memory will be displayed instead.

I007 The counting variable AD is set to have a value of 3, and the starting address which is loaded into the display DMA is the starting address of the reference spectrum which was identified by thumbwheel switches 36 at the time that the display button 40 was depressed. Program flow then continues with step I008.

I008 The microprocessor provides a device select control signal which is operative to reset the ramp generator 312 (FIG. 10). This concludes the interrupt routine. From here, the program jumps back into the main body of the program at the point at which it was interrupted.

In summary, then, a portable element analysis unit has been described which provides qualitative and quantative analysis of mineral or other material specimens of unknown compositions. This portable unit provides storage of reference spectrums, as well as storage of sample spectrums which have been obtained by the operator. The element analysis unit provides a visual display of the various spectrums, each of which represents the energy distribution of fluorescent particles emitted by a mineral sample under study. A visual cursor is provided by heightening the intensity of one energy channel of the displayed spectrum. This cursor may be moved by the operator to occupy any one of the energy channels therealong. The unit provides a read-out of the symbol of the element having its principal peak at the position identified by the cursor. Channels corresponding to any secondary peaks in the spectrum of that element are indicated to the operator by heightening the intensity of the spectrum in those channels as well. This permits the operator to readily ascertain whether or not that element is present in the mineral sample being tested. The element analysis unit also provides a read-out of the concentration of the particular element within the sample being studied. Enhancement of the displayed spectrum may be provided so as to emphasize peaks thereon, with a smoothing function being provided so as to reduce the effect of statistical outliers along the spectrum. Furthermore, a normalization function allows the operator to normalize the amplitude of the spectrum in accordance with the number of counts in the backscatter peak channel.

In the embodiment which has been described, it has been presumed that sufficient storage space exists within the memory in the element analysis unit to permit storage of a very large number of look-up tables. The large majority of this space will be utilized to read-out the concentration of the element under study. The amount of storage space required to implement this function may be reduced as required, however. One technique of reducing this amount of storage space would be to provide look up tables only for selected elements, or only for selected mineral compositions. Another technique which could be utilized would be to provide an appropriate amount of read-only memory within each of the sensor heads, so as to provide look-up tables specifically associated with the detectors included in that sensor head. In this fashion, interchanging of the sensor head would automatically entail changing of the look-up tables in accordance with the particular detectors employed in the new sensor head. Furthermore, the concentration function could be deleted entirely. Then, written look-up tables could be provided to the operator. The operator could thus determine concentration of a particular element by referring to an appropriate look-up table, and using the ratio value provided by the unit to index the table.

Therefore, although the invention has been described with respect to a preferred embodiment, it is apparent that many rearrangements and alterations of the parts may be made without departing from the spirit and scope of the present invention, as defined in the appended claims.

What is claimed is:

1. An element analysis unit comprising:
    sensor means including radiation means for irradiating a material to be analyzed, detector means for detecting radiation returned by said irradiated material and providing signals representative of said returned radiation, and means for providing an indication as to the type of said radiation means and said detector means included in said sensor means;
    means for interconnecting said sensor means to a processing means; and
    processing means for processing said signals representative of said returned radiation and responsive to said indication for adapting said processing in accordance with the type of said radiation means and said detector means included in said sensor means interconnected with said processing means, whereby sensor means having different said radiation means and/or different said detector means may be interconnected with said processing means and said processing means will be automatically adapted for operation therewith.

2. An element analysis unit as set forth in claim 1 wherein said sensor means includes a plurality of detector means, and means for selecting one of said detectors for use in detecting said radiation returned from said irradiated material and wherein said indicating means includes sensor identification means identifying that sensor means and detector identification means identifying which of said plurality of detector means is presently being selected by said means for selecting.

3. An element analysis unit as set forth in claim 1, wherein said unit further comprises means controlled by said processing means for displaying at least a portion of the energy spectrum of said radiation returned from said irradiated material, said spectrum including a backscatter peak resulting from radiation scattered back to said detector from said radiation means, and wherein said processing means includes means for determining the location of said backscatter peak through reference to said indication, for calculating the integral of the backscatter peak thus located, and for normalizing said spectrum in accordance with a factor substantially proportionate to said integral.

4. An element analysis unit as set forth in claim 1, and further comprising means responsive to calibration control signals supplied by said processing means for controlling the calibration of said detector means, said processing means supplying calibration control signals selected in accordance with said indication.

5. An element analysis unit as set forth in claim 4, wherein said means for controlling said calibration comprises means for controlling the gain of said signals representative of said returned radiation.

6. Apparatus as set forth in claim 4, wherein said detector means comprises a proportional counter tube providing output signals having amplitudes dependent upon the magnitude of the voltage being applied across said proportional counter tube, and wherein said calibration control means comprises voltage means for applying a selected voltage across said proportional counter tube in accordance with said calibration control signals.

7. Apparatus as set forth in claim 4, wherein said calibration control means comprises means for adjusting the DC level of said signals provide by said detector means in accordance with said calibration control signals.

8. An element analysis unit as set forth in claim 1, wherein said processing means comprises means for accumulating a spectrum generally indicating the energy distribution of said returned radiation, said spectrum including a backscatter peak resulting from radiation scattered back to said detector from said radiation means, for locating said backscatter peak through reference to said indication, and for utilizing the backscatter peak thus located in the processing of said signals representative of said returned radiation.

9. An element analysis unit as set forth in claim 8, further comprising means for manually selecting a portion of said spectrum which is of interest, wherein said processing means calculates the ratio of the amplitude of the located backscatter peak to the amplitude of said selected portion of said spectrum and provides said calculated ratio to a display means, and wherein said unit further comprises display means for displaying said calculated ratio.

10. An element anaylsis unit as set forth in claim 9, and further comprising memory means having element concentration values for various calculated ratios stored therein at addressable locations, and wherein said processing means addresses said memory means in accordance with said calculated ratio so as to retrieve a corresponding said element concentration value.

11. An element analysis unit as set forth in claim 1, wherein said unit further comprises means for displaying the energy spectrum of said radiation returned from said irradiated material and means controlled by said processing means for identifying features of said energy spectrum, the identity of said features being different for different said radiation means and detector means, wherein said processing means is responsive to said indication to control said identifying means to correctly identify features of said spectrum in accordance with the radiation means and detector means included in said sensor means.

12. An element analysis unit as set forth in claim 11, further comprising means for selecting a portion of said spectrum for identification, wherein said identifying means includes means for displaying an indication of which element, if any, has its major spectral peak within the portion of said spectrum selected by said selecting means.

13. Apparatus as set forth in claim 12, wherein said display means also displays a cursor identifying a portion on said spectrum and movable with respect to said spectrum such that said identified point on said spectrum is movable along said spectrum, and wherein said means for selecting a portion of said spectrum for identification comprises cursor control means for controlling the location of said cursor and thus said identified portion.

14. Apparatus as set forth in claim 13, wherein said means for displaying an indication comprises alphanumeric display means for displaying the chemical symbol of the element, if any, which has its major spectral peak within the portion on the displayed spectrum identified by said cursor.

15. Apparatus comprising:
a housing having an opening therein;
radiation means mounted within said housing for irradiating a material through said opening;
detector means also mounted within said housing for detecting radiation returned from said irradiated material, and passing through said opening, said detector means providing signals having values representative of the energy of said returned radiation detected thereby;
calibration means selectively operable for controlling said detector means to adjust the relationship between said values of said signals and the energy of said detected radiation;
shutter means for selectively blocking said opening in said housing to prevent the passage of radiation therethrough, so that a surface of said shutter is irradiated by said radiation means when said shutter means is blocking said opening and that said detector means then detects radiation returned from said surface of said shutter, said surface being formed of a material having a fluorescent radiation characteristic selected so that said signals provided by said detector means will have a known distribution of values; and
means for automatically controlling said calibrating means, when said shutter is blocking said opening, said means being operative to accumulate a spectrum indicating the actual distribution of said values of said signals, to compare said spectrum with said known distribution of values, and to operate said calibration means so as to eliminate any differences between said actual distribution and said known distribution, whereby said detector means is automatically calibrated.

16. Apparatus as set forth in claim 15, wherein said calibration means comprises means for controlling the gain of said signals provided by said detector means.

17. Apparatus as set forth in claim 15, wherein said calibration means comprises means for controlling the offset of said signals provided by said detector means.

18. Apparatus as set forth in claim 15, wherein said calibration means comprises means for controlling both the gain and offset of said signals provided by said detector means.

19. Apparatus as set forth in claim 15, wherein said detector means comprises a proportional counter providing an output signal whose gain is dependent upon the magnitude of the voltage applied across said proportional counter, and wherein said calibration means comprises means for controlling the magnitude of the voltage being applied across said proportional counter.

20. Apparatus as set forth in claim 19, wherein said means for controlling the magnitude of the voltage being applied across said proportional counter comprises a programmable high voltage supply whose high voltage output is applied across said proportional counter.

21. Apparatus as set forth in claim 19, wherein said calibration control means further comprises means for adding a controllable offset signal into said output signal being provided by said proportional counter, and wherein said means for automatically controlling said calibration means comprises means for controlling both said voltage controlling means and said offset signal adding means, whereby both the gain and the offset of said proportional counter output signal are controlled.

22. A method of calibrating a system including a housing having an opening therein, radiation means mounted within said housing for irradiating a material through said opening, detector means also mounted within said housing for detecting radiation returned from said irradiated material and passing through said opening, said detector means providing signals having values representative of the energy of said returned radiation detected thereby, calibration means selectively operable for controlling said detector means to adjust the relationship between said values of said signals and the energy of said detected radiation, shutter means for selectively blocking said opening in said housing to prevent the passage of radiation therethrough so that a surface of said shutter is irradiated by said radiation means when said shutter means is blocking said opening and that said detector means then detects radiation returned from said surface of said shutter, said surface being formed of a material having a fluorescent radiation characteristic selected so that said signals provided by said detector means will have a known distribution of values, said method comprising the steps of:

blocking said opening with said shutter;

accumulating a spectrum indicating the actual distribution of values of said signals;

comparing said accumulated distribution with said known distribution; and operating said calibrating means so as to eliminate any difference between said actual distribution and said known distribution, whereby said detector means is calibrated.

23. Apparatus comprising visual display means for providing an at least two dimensional visual display, control means for controlling said visual display means to provide a visual representation of a selected fluorescent radiation spectrum, and to provide a visual indication identifying a selected portion of said visual representation, said control means being responsive to a cursor control signal for controlling the position of said visual indication on said visual display;

cursor control means for providing said cursor control signal, said cursor control means being manually operable such that the position of said visual indication on said visual display is manually controllable, and means for providing a visual display of an element indication representing a selected atomic element wherein said control means further controls said element display means so as to display the said element indication representing the atomic element, if any, having its major spectral peak at the position along said visual representation identified by said visual indication.

24. Apparatus as set forth in claim 23 wherein said control means includes means for controlling said visual display means to provide secondary visual indications identifying portions of said visual representation corresponding to the locations of all of the other spectral peaks of the fluorescent radiation spectrum of said atomic element, if any, having its major spectral peak at the position along said visual representation identified by said visual indication.

25. Apparatus as set forth in claim 23, wherein said control means includes means for controlling said visual display means to display at least two said spectrums at once, whereby said spectrums may be compared one with another.

26. Apparatus as set forth in claim 23, wherein said control means comprises computer means programmed to control said visual display means and said means for providing a visual display of said element indication.

27. Apparatus comprising:

a housing having an opening therein;

radiation means mounted within said housing for irradiating a material through said opening;

detector means also mounted within said housing for detecting radiation returned from said irradiated material, and passing through said opening, said detector means providing signals in accordance with said returned radiation detected thereby;

shutter means for selectively blocking said opening in said housing to prevent the passage of radiation therethrough, so that a surface of said shutter means is then irradiated by said radiation means and that said detector means then detects radiation returned from said surface of said shutter, said surface being formed of a material having a known flourescent radiation characteristic;

means responsive to said detector signals for providing output signals having values related to the energy of said returned radiation detected by said detector means;

calibration means selectively operable for controlling the relationship between the values of said output signals and the energy of said returned radiation detected by said detector means; and means for automatically controlling said calibrating means when said shutter is blocking said opening, said means being operative to compare the flourescent radiation characteristic represented by said output signals provided by said processing means with said known flourescent radiation characteristic and to operate said calibration means so as to eliminate any difference between said characteristics, whereby said detector means is automatically calibrated.

* * * * *